(12) United States Patent
Gao et al.

(10) Patent No.: US 8,338,580 B2
(45) Date of Patent: Dec. 25, 2012

(54) FLUORESCENT PROTEIN MOLECULES

(76) Inventors: Xiaolian Gao, Houston, TX (US);
Jinchun Wang, Houston, TX (US)

( * ) Notice: Subject to any disclaimer, the term of this patent is extended or adjusted under 35 U.S.C. 154(b) by 256 days.

(21) Appl. No.: 12/592,940

(22) Filed: Dec. 4, 2009

(65) Prior Publication Data

US 2010/0286370 A1    Nov. 11, 2010

Related U.S. Application Data

(60) Provisional application No. 61/201,034, filed on Dec. 5, 2008.

(51) Int. Cl.
  *C07H 21/04*   (2006.01)
  *A61K 38/00*   (2006.01)
(52) U.S. Cl. .................................. 536/23.1; 530/350
(58) Field of Classification Search ....................... None
  See application file for complete search history.

*Primary Examiner* — Anand Desai
*Assistant Examiner* — Samuel Liu
(74) *Attorney, Agent, or Firm* — G. Kenneth Smith

(57) ABSTRACT

The present invention relates to novel fluorescent proteins and to methods of making these proteins and the uses thereof.

1 Claim, 14 Drawing Sheets

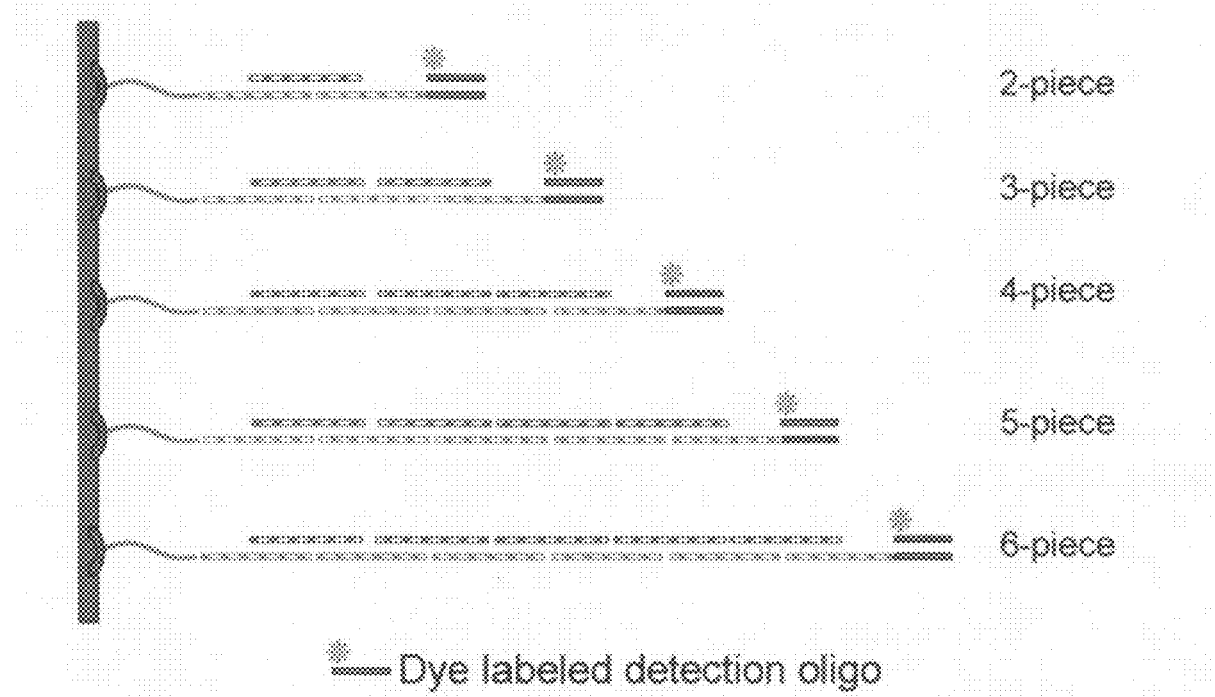

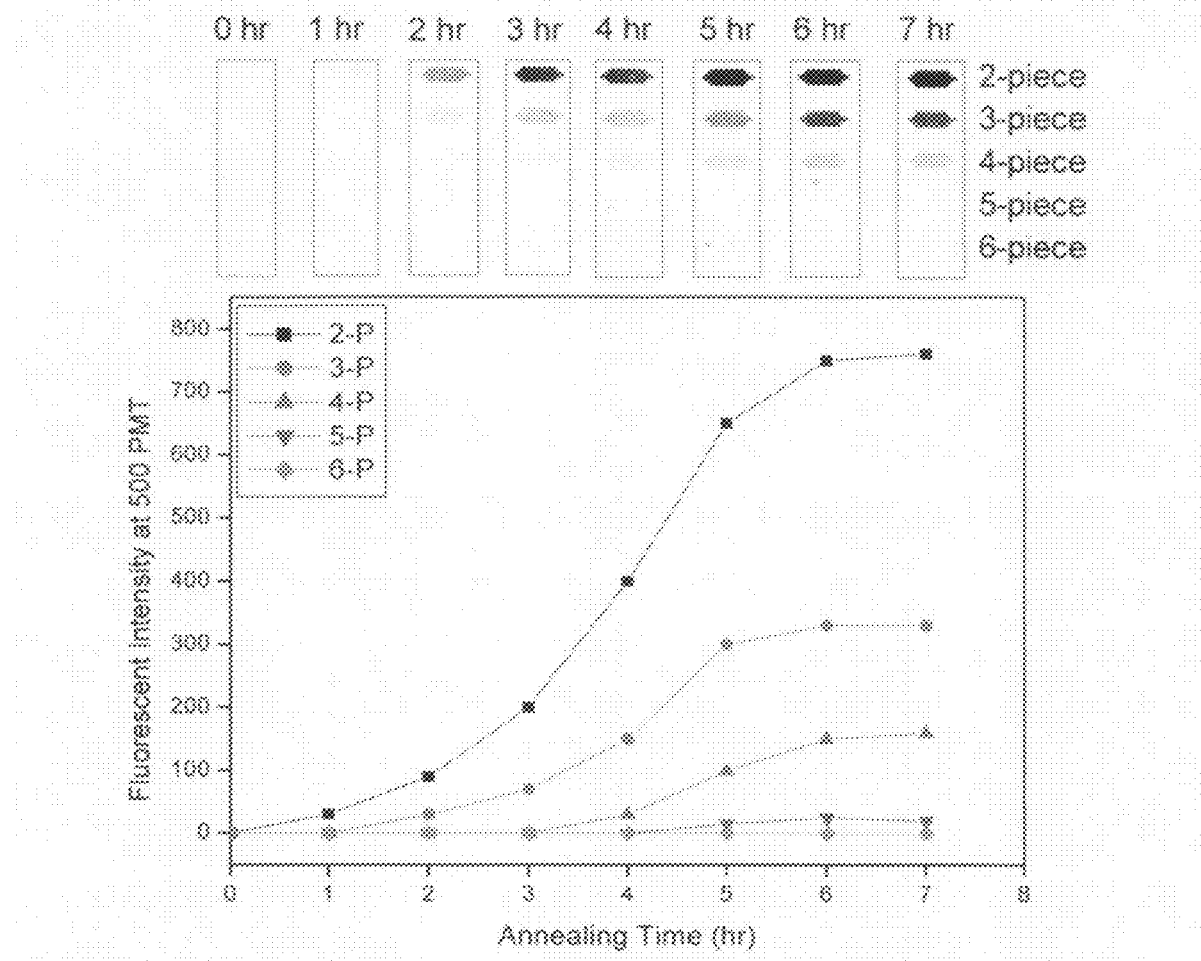

Figure 5A

2G2
ATGAGCAAAGGCGAAGAACTGTTCACCGGTGTGGTGCCGATCCTGGTGGAAC
TGGATGGCGATGTGAACGGCCAGAAGTTCAGCGTGAGCGGCGAAGGCGAAG
GCGATGCGACCTATGGCAAACTGACCCTGAAGTTCATCTGCACCACCGGCAA
ACTGCCGGTGCCGTGGCCGACCCTGGTGACCACCCTGGGCTATGGCCTGCAG
TGCTTCGCGCGCTATCCGGATCATATGAAACAGCATGATTTCTTCAAGAGCGC
GATGCCGGAAGGCTATGTGCAGGAACGCACCATCTTCTTCAAAGATGATGGC
AACTACAAGACCCGCGCGGAAGTGAAATTCGAAGGCGATACCCTGGTGAAC
CGCATCGAACTGAAAGGCATCGATTTCAAAGAAGATGGCAACATCCTGGGCC
ATAAACTGGAATACAACTATAACAGCCATAACGTGTATATCACCGCGGATAA
ACAGAAGAACGGCATCAAAGCGAACTTCAAAATCCGCCATAACATCGAAGA
TGGCAGCGTGCAGCTGGCGGATCATTATCAGCAGAACACCCCGATCGGCGAT
GGCCCGGTGCTGCTGCCGGATAACCATTATCTGAGCACCCAGAGCGCGCTGA
GCAAAGATCCGAACGAGAAACGCGATCATATGGTGCTGCTGGAATTCGTGAC
CGCAGCGGGCATCACCCATGGCATGGATGAACTGTACAAG (SEQ ID NO. 1)

2B11
ATGAGCAAAGGCGAAGAACTGTTCACCGGCGTGGTGCCGATCCTGGTGGAAC
TGGATGGCGATGTGAACGGCCATAAGTTCAGCGTGAGCGGCGAAGGCGAAG
GCGATGCGACCTATGGCAAACTGACCCTGAAGTTCATCTGCACCACCGGCAA
ACTTCCCGTGCCCTGGCCCACCCTCGTGACCACCCTGACCTACGGCGTGCAGT
GCTTCAGCCGCTATCCGGATCATATGAAACAGCATGATTTCTTCAAGAGCGC
GATGCCGGAAGGCTATGTGCAGGAACGCACCATCTTCTACAAAGATGATGGC
AACTACAAGACCCGTGCGGAAGTGAAGTTCGAAGGCGATACCCTGGTGAACC
GCATCGAACTGAAAGGCATCGATTTCAAAGAAGATGGCAACATCCTGGGCCA
TAAAATGGAATACAACTTCAACAGCCATAACGTGTATATCATGGGCGATAAA
CCGAAAAACGGCATCAAAGTGAACTTCAAAATCCGCCATAACATCAAAGATG
GCGGCGTACAGCTGGCGGATCATTATCAGCTGAACACTCCGATCGGCGATGG
CCCAGTGATCCTGCCGGATAACCATTATCTGAGCACCCAGAGCGCGCTGAGC
AAAGATCCGAACGAGAAACGCGATCATATGGTGCTGCTGGAATTCGTGACCG
CAGCTCGCATCACCCATGGCATGGATGAACTGTACAAG (SEQ ID NO. 2)

E6
ATGAGCAAAGGCGAAGAAGATAACATGGCGATCATCAAAGAGTTCATGCGC
TTCAAAGTGCGCATGGAAGGCAGCGTGAACGGCCATGAATTCGAAATCGAAG
GTGAAGGTGAAGGCCGCCCGTATGAAGGCACCCAGACCGCGAAACTGAAAG
TGACCAAAGGCGGTCCGCTGCCGTTCGCGTGGGATATCCTGAGCCCGCAGTT
CTGCTATGGCAGCAAAGCGTATGTGAAACATCCGGCGGATATCCCGGATTAC
TTCAAACTGAGCTTCCCGGAAGGCTTCAAATGGGAACGCATGATGAACTTCG
AAGATGGCGGTGTGGTGACCGTGACCCAGGATAGCAGCCTGCAGGATGGCG
AATTCATCTACAAAGTGAAACTGCGCGGCACCAACTTCCCGAGCGATGGCCC
GGTGATGCAGAAAAAGACCATGGGCTGGGAAGCGAGCAGCGAACGCATGTA
TCCGGAAGATGGCGCACTGAAAGGCGAAATCAAACAGCGCCTGAAACTGAA
AGATGGCGGTCATTATGATGCGGAAGTGAAAACCACCTATAAAGCGAAAAA

Figure 5B

GCCGGTGCAGCTGCCGGGTGCCTATAACGTGAACATCAAACTGGATATCACC
AGCCATAACGAAGATTATACCATCGTGGAACAGTATGAACGCGCGGAAGGCC
GCCATAGCACCGGCGGCATGGATGAACTGTACAAG (SEQ ID NO. 3)

1H10
ATGAGCAAAGGCGAAGAGAACAACATGGCGATCATCAAAGAGTTCATGCGC
TTCAAAGTGCGCATGGAAGGCAGCGTGAACGGCCATGAATTCGAAATCGAAG
GTGAAGGTGAAGGCCGTCCGTATGAAGGCACCCAGACCGCGAAACTGAAAG
TGACCAAAGGCGGCCCGCTGCCGTTCGCGTGGGATATCCTGAGCCCGCAGTT
CACCTATGGCAGCAAAGCGTATGTGAAACATCCGACCGGCATCCCGGATTAC
TTCAAACTGAGCTTCCCGGAAGGCTTCAAATGGGAACGCGTGATGAACTTCG
AAGATGGCGGTGTGGTGACCGTGACCCAGGATAGCAGCCTGCAGGATGGCG
AATTCATCTACAAAGTGAAACTGCGCGGCACCAACTTCCCGAGCGATGGCCC
GGTGATGCAGAAAAAGACCATGGGCTGGGAAGCGAGCAGCGAACGCATGTA
TCCGGAAGATGGCGCGCTGAAAGGCGAAATCAAGATGCGCCTGAAACTGAA
AGATGGCGGCCATTATAGCGCGGAAACCAAAACCACCTACAAAGCGAAGAA
ACCGGTGCAGCTGCCGGGTGCGTATATCGTGGGCATCAAACTGGATATCACC
AGCCATAACGAAGATTATACCATCGTGGAACAGTATGAACGTGCGGAAGGCC
GCCATAGCACCGGTGGCATGGATGAACTGTACAAG (SEQ ID NO. 4)

1H3
ATGAGCAAAGGCGAAGAAGATAACATGGCGATCATCAAAGAGTTCATGCGC
TTCAAATTGCGCATGGAAGGCAGCGTTAACGGCCATGAATTCGAAATCGAAG
GCGAAGGCGAAGGCCGTCCGTATGAAGGCACCCAGACCGCGAAACTGAAAG
TGACCAAAGGCGGTCCGCTGCCGTTCGCGTGGGATATCCTGAGCCCGCAGTT
CTGCTATGGCAGCAAAGCGTATGTGAAACATCCGACCGGCATCCCGGATTAC
TTCAAACTGAGCTTCCCGGAAGGCTTCAAATGGGAACGCATGATGAACTTCG
AAGATGGCGGTGTGGTGACCGTGACCCAGGATAGCAGCCTGCAGGATGGCG
AATTCATCTACAAAGTGAAACTACGCGGCACCAACTTCCCGAGTGATGGCCC
GGTGATGCAGAAAAAGACCATGGGCTGGGAAGCGAGCAGCGAACGCATGTA
TCCGGAAGATGGCGCGCTGAAAGGCGAAATCAAGATGCGCCTGAAACTGAA
AGATGGCGGCCATTATAGCGCGGAAACCAAAACCACCTACAAAGCGAAGAA
ACCGGTGCAGCTGCCGGGTGCGTATATCGTGGGCATCAAACTGGATATCACC
AGCCATAACGAAGATTATACCATCGTGGAACAGTATGAACGTGCGGAAGGCC
GCCATAGCACCGGTGGCATGGATGAACTGTACAAG (SEQ ID NO. 5)

Figure 6

2G2
MSKGEELFTGVVPILVELDGDVNGQKFSVSGEGEGDATYGKLTLKFICTTGKLPV
PWPTLVTTLGYGLQCFARYPDHMKQHDFFKSAMPEGYVQERTIFFKDDGNYKT
RAEVKFEGDTLVNRIELKGIDFKEDGNILGHKLEYNYNSHNVYITADKQKNGIKA
NFKIRHNIEDGSVQLADHYQQNTPIGDGPVLLPDNHYLSTQSALSKDPNEKRDH
MVLLEFVTAAGITHGMDELYK (SEQ ID NO. 6)

2B11
MSKGEELFTGVVPILVELDGDVNGHKFSVSGEGEGDATYGKLTLKFICTTGKLPV
PWPTLVTTLTYGVQCFSRYPDHMKQHDFFKSAMPEGYVQERTIFYKDDGNYKT
RAEVKFEGDTLVNRIELKGIDFKEDGNILGHKMEYNFNSHNVYIMGDKPKNGIK
VNFKIRHNIKDGGVQLADHYQLNTPIGDGPVILPDNHYLSTQSALSKDPNEKRDH
MVLLEFVTAARITHGMDELYK (SEQ ID NO. 7)

E6
MSKGEEDNMAIIKEFMRFKVRMEGSVNGHEFEIEGEGEGRPYEGTQTAKLKVTK
GGPLPFAWDILSPQFCYGSKAYVKHPADIPDYFKLSFPEGFKWERMMNFEDGGV
VTVTQDSSLQDGEFIYKVKLRGTNFPSDGPVMQKKTMGWEASSERMYPEDGAL
KGEIKQRLKLKDGGHYDAEVKTTYKAKKPVQLPGAYNVNIKLDITSHNEDYTIV
EQYERAEGRHSTGGMDELYK (SEQ ID NO. 8)

1H10
MSKGEENNMAIIKEFMRFKVRMEGSVNGHEFEIEGEGEGRPYEGTQTAKLKVTK
GGPLPFAWDILSPQFTYGSKAYVKHPTGIPDYFKLSFPEGFKWERVMNFEDGGV
VTVTQDSSLQDGEFIYKVKLRGTNFPSDGPVMQKKTMGWEASSERMYPEDGAL
KGEIKMRLKLKDGGHYSAETKTTYKAKKPVQLPGAYIVGIKLDITSHNEDYTIVE
QYERAEGRHSTGGMDELYK (SEQ ID NO. 9)

1H3
MSKGEEDNMAIIKEFMRFKLRMEGSVNGHEFEIEGEGEGRPYEGTQTAKLKVTK
GGPLPFAWDILSPQFCYGSKAYVKHPTGIPDYFKLSFPEGFKWERMMNFEDGGV
VTVTQDSSLQDGEFIYKVKLRGTNFPSDGPVMQKKTMGWEASSERMYPEDGAL
KGEIKMRLKLKDGGHYSAETKTTYKAKKPVQLPGAYIVGIKLDITSHNEDYTIVE
QYERAEGRHSTGGMDELYK (SEQ ID NO. 10)

FIGURE 7

EBFP

MSKGEELFTGVVPILVELDGDVNGHKFSVSGEGEGDATYGKLTLKFICTTGKLPVPWPTLVTTLTHGVQCFSRYPDHMKQHDFFKSAMPEGYVQERTIFFKDDGNYKTR
AEVKFEGDTLVNRIELKGIDFKEDGNILGHKLEYNFNSHNVYIMADKQNGIKVNFKIRHNIED (SEQ ID 11)

T-Sapphire

MSKGEELFTGVVPVLVELDGDVNGQKFSVSGEGEGDATYGKLTLNFICTTGKLPVPWPTLVTTFSYGVMVFARYPDHMKQHDFFKSAMPEGYVQERTIFYKDDGNYKT
RAEVKFEGDTLVNRIELKGIDFKEDGNILGHKMEYNFNSHNVYIMGDKPKNGIKANFKIRHNIKDGGVQLADHYQQNTPIGDGPVLLPDNHYLSIQSALSKDPNEKRDH
MILLEFVTAARITHGMDELYK (SEQ ID 12)

Cerulean

MSKGEELFTGVVPILVELDGDVNGHKFSVSGEGEGDATYGKLTLKFICTTGKLPVPWPTLVTTLTWGVQCFARYPDHMKQHDFFKSAMPEGYVQERTIFFKDDGNYKT
RAEVKFEGDTLVNRIELKGIDFKEDGNILGHKLEYNAISDIVYITADKQKNGIKANFKIRHNIEDGSVQLADHYQQNTPIGDGPVLLPDNHYLSTQSALSKDPNEKRDHMV
LLEFVTAAGITLGMDELYK (SEQ ID 13)

ECFP

MSKGEELFTGVVPILVELDGDVNGHKFSVSGEGEGDATYGKLTLKFICTTGKLPVPWPTLVTTLTWGVQCFARYPDHMKQHDFFKSAMPEGYVQERTIFFKDDGNYKT
RAEVKFEGDTLVNRIELKGIDFKEDGNILGHKLEYNAISDIVYITADKQKNGIKANFKIRHNIEDGSVQLADHYQQNTPIGDGPVLLPDNHYLSTQSALSKDPNEKRDHMV
LLEFVTAAGITLGMDELYK (SEQ ID 14)

CyPet

MSKGEELFGGVIPVLVELEGDVNGQKFSVSGEGEGDATYGKLTLNFICTTGKLPVPWPTLVTTLTWGVQCFSRYPDHMKQHDFFKSVMPEGYVQERTIFYKDDGNYKT
RAEVKFEGDTLVNRIELKGIDFKEDGNILGHKMEYNYNSHIVYITGDKPKNGIKANFKARHNIKDGSVQLADHYQQNTPIGDGPVILPDNHYLSTQSALSKDPNEKRDHM
ILLEFVTAARITHGMDELYK (SEQ ID 15)

WtGFP

CONTINUED FROM FIG. 7

MSKGEELFTGVVPILVELDGDVNGHKFSVSGEGEGDATYGKLTLKFICTTGKLPVPWPTLVTTFSYGVQCFSRYPDHMKQHDFFKSAMPEGYVQERTIFFKDDGNYKTR
AEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHM
VLLEFVTAAGITHGMDELYK (SEQ ID 16)

EGFP

MSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTR
AEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHM
VLLEFVTAAGITLGMDELYK (SEQ ID 17)

TOPAZ

MSKGEELFTGVVPILVELDGDVNGHKFSVSGEGEGDATYGKLTLKFICTTGKLPVPWPTLVTTLGHGVQCFARYPDHMRQHDFFKSAMPEGYVQERTIFFKDDGNYKT
RAEVKFEGDTLVNRIELKGIDFKEDGNILKLEYNFNSHNVYIMADKQKNGIKANFKIRHNIEDGSVQLADHYQQNTPIGDGPVLLPDNHYLSYQSALSKDPNEKRDH
MVLLEFVTAAGITLGMDELYK (SEQ ID 18)

EYFP

MSKGEELFTGVVPILVELDGDVNGHKFSVSGEGEGDATYGKLTLKFICTTGKLPVPWPTLVTTFGYGLQCFARYPDHMKQHDFFKSAMPEGYVQERTIFFKDDGNYKTR
AEVKFEGDTLVNRIELKGIDFKEDGNILGHKLEYNYNSHNVYIMADKQKNGIKVNFKIRHNIEDGSVQLADHYLSYQSALSKDPNEKRDHM
VLLEFVTAAGITLGMDELYK (SEQ ID 19)

VENUS

MSKGEELFTGVVPILVELDGDVNGHKFSVSGEGEGDATYGKLTLKLICTTGKLPVPWPTLVTTLGYGLQCFARYPDHMKQHDFFKSAMPEGYVQERTIFFKDDGNYKTR
AEVKFEGDTLVNRIELKGIDFKEDGNILGHKLEYNYNSHNVVITADKQKNGIKANFKIRHNIEDGGVQLADHYQQNTPIGDGPVLLPDNHYLSYQSALSKDPNEKRDHMV
LLEFVTAAGITHGMDELYK (SEQ ID 20)

mCitrine

CONTINUED FROM FIG. 7

MSKGEELFTGVVPVLVELDGDVNGQKFSVSGEGEGDATYGKLTLNFICTTGKLPVPWPTLVTTFGYGLMCFARYPDHMKQHDFFKSAMPEGYVQERTIFYKDDGNYKT
RAEVKFEGDTLVNRIELKGIDFKEDGNILGHKMEYNYNSHNVYIMGDKPKNGIKVNFKIRHNIKDGSVQLADHYQQNTPIGDGPVLLPDNHYLSYQSKLSKDPNEKRDH
MILLEFVTAARITHGMDELYK (SEQ ID 21)

YPET

MSKGEELFTGVVPVLVELDGDVNGQKFSVSGEGEGDATYGKLTLNLLCTTGKLPVPWPTLVTTLGYGVQCFARYPDHMKQHDFFKSAMPEGYVQERTIFYKDDGNYK
TRAEVKFEGDTLVNRIELKGIDFKEDGNILGHKMEYNYNSHNVYITGDKPKNGIKANFKIRHNIKDGGVQLADHYQQNTPIGDGPVLLPDNHYLSYQSALFKDPNEKRDH
MILLEFLTAARITEGMNELYK (SEQ ID 22)

mBanana

MSKGEENNMAVIKEFMRFKVRMEGSVNGHEFEIEGEGEGRPYEGTQTAKLKVTKGGPLPFAWDILSPQFCYGSKAYVKHPTGIPDYFKLSFPEGFKWERVMNFEDGG
VVTVAQDSSLQDGEFIYKVKLRGTNFPSDGPVMQKKTMGWEASSERMYPEDGALKGEIKMRLKLKDGGHYSAETKTTYKAKPVQLPGAYIAGEKIDITSHNEDYTIVE
LYERAEGRHSTGGMDELYK (SEQ ID 23)

mOrange

MSKGEENNMAIIKEFMRFKVRMEGSMNGHEFEIEGEGEGRPYEGTQTAKLKVTKGGPLPFAWDILSPQFTYGSKAYVKHPADIPDYFKLSFPEGFKWERVMNFEDGGV
VTTVTQDSSLQDGEFIYKVKLRGTNFPSDGPVMQKKTMGWEASSERMYPEDGALKGEIKMRLKLKDGGHYTSEVKTTYKAKKPVQLPGAYIVGIKLDITSHNEDYTIVEQ
YERAEGRHSTGGMDELYK (SEQ ID 24)

dTomato

MSKGEEVIKEFMRFKVRMEGSMNGHEFEIEGEGEGRPYEGTQTAKLKVTKGGPLPFAWDILSPQFMYGSKAYVKHPADIPDYKKLSFPEGFKWERVMNFEDGGLVTV
TQDSSLQDGTLIYKVKMRGTNFPPDGPVMQKKTMGWEASTERLYPRDGVLKGEIHQALKLKDGGHYLVEFKTIYMAKKPVQLPGYYYVDTKLDITSHNEDYTIVEQYER
SEGRHHLFLYGMDELYK (SEQ ID 25)

mStrawberry

CONTINUED FROM FIG. 7

MSKGEENNMAIIKEFMRFKVRMEGSVNGHEFEIEGEGEGRPYEGTQTAKLKVTKGGPLPFAWDILTPNFTYGSKAYVKHPADIPDYLKLSFPEGFKWERVMNFEDGGV
VTVTQDSSLQDGEFIYKVKLRGTNFPSDGPVMQKTMGWEASSERMYPEDGALKGEIKMRLKLKDGGHYDAEVKTTYKAKKPVQLPGAYIVGIKLDITSHNEDYTIVEL
YERAEGRHSTGGMDELYK (SEQ ID 26)

mCherry

MSKGEEDNMAIIKEFMRFKVHMEGSVNGHEFEIEGEGEGRPYEGTQTAKLKVTKGGPLPFAWDILSPQFMYGSKAYVKHPADIPDYLKLSFPEGFKWERVMNFEDGG
VVTVTQDSSLQDGEFIYKVKLRGTNFPSDGPVMQKTMGWEASSERMYPEDGALKGEIKQRLKLKDGGHYDAEVKTTYKAKKPVQLPGAYNVNIKLDITSHNEDYTIVE
QYERAEGRHSTGGMDELYK (SEQ ID 27)

2B11

MSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFYKDDGNYKTR
AEVKFEGDTLVNRIELKGIDFKEDGNILGHKMEYNFNSHNVYIMGDKPKNGIKVNFKIRHNIKDGGVQLADHYQLNTPIGDGPVILPDNHYLSTQSALSKDPNEKRDHM
VLLEFVTAARITHGMDELYK (SEQ ID 28)

2G2

MSKGEELFTGVVPILVELDGDVNGQKFSVSGEGEGDATYGKLTLKFICTTGKLPVPWPTLVTTLGYGLQCFARYPDHMKQHDFFKSAMPEGYVQERTIFFKDDGNYKTR
AEVKFEGDTLVNRIELKGIDFKEDGNILGHKLEYNYNSHNVYITADKQKNGIKANFKIRHNIEDGSVQLADHYQQNTPIGDGPVLLPDNHYLSTQSALSKDPNEKRDHMV
LLEFVTAAGITHGMDELYK (SEQ ID 29)

E6

MSKGEEDNMAIIKEFMRFKVRMEGSVNGHEFEIEGEGEGRPYEGTQTAKLKVTKGGPLPFAWDILSPQFCYGSKAYVKHPADIPDYFKLSFPEGFKWERMMNFEDGG
VVTVTQDSSLQDGEFIYKVKLRGTNFPSDGPVMQKKTMGWEASSERMYPEDGALKGEIKQRLKLKDGGHYDAEVKTTYKAKKPVQLPGAYNVNIKLDITSHNEDYTIVE
QYERAEGRHSTGGMDELYK (SEQ ID 30)

1H10

CONTINUED FROM FIG. 7

REPLACEMENT SHEET

MSKGEENNMAIIKEFMRFKVRMEGSVNGHEFEIEGEGEGRPYEGTQTAKLKVTKGGPLPFAWDILSPQFTYGSKAYVKHPTGIPDYFKLSPEGFKWERVMNFEDGGV
VTVTQDSSLQDGEFIYKVKLRGTNFPSDGPVMQKKTMGWEASSERMYPEDGALKGEIKMRLKLKDGGHYSAETKTTYKAKKPVQLPGAYIVGIKLDITSHNEDYTIVEQ
YERAEGRHSTGGMDELYK (SEQ ID 31)

1H3

MSKGEEDNMAIIKEFMRFKLRMEGSVNGHEFEIEGEGEGRPYEGTQTAKLKVTKGGPLPFAWDILSPQFCYGSKAYVKHPTGIPDYFKLSPEGFKWERMMNFEDGGV
VTVTQDSSLQDGEFIYKVKLRGTNFPSDGPVMQKKTMGWEASSERMYPEDGALKGEIKMRLKLKDGGHYSAETKTTYKAKKPVQLPGAYIVGIKLDITSHNEDYTIVEQ
YERAEGRHSTGGMDELYK (SEQ ID 32)

2H1

MSKGEELFTGVVPILVELDGDVNGHKFSVSGEGEGDATYGKLTLNFICTTGKLPVPWPTLVTTFGYGLMCFARYPDHMKQHDFFKSAMPEGYVQERTIFYKDDGNYKT
RAEVKFEGDTLVNRIELKGIDFKEDGNILGHKLEYNAISDIVYITADKQNGIKANFKIRHNIEDGSVQLADHYQQNTPIGDGPVLLPDNHYLSTQSALSKDPSEKRDHMVL
LEFVTAAGITLGMDELYK (SEQ ID 33)

1H11

MSKGEELFTGVVPILVELDSDVNGHKFSVSGEGEGDATYGKLTLNFICTTGKLPVPWPTLVTTLGHCVQCFARYPDHMRQHDFFKSAMPEGYVQERTIFFKDDGNYKTR
AEVKFEGDTLVNRIELKGIDFKEDGNILGHKLEYNAISDIVYITADKQKNGIKANFKIRHNIKDGGVQLADHYQQNTPIGDGPVLLPDNHYLSTQSALSKDPNEKRDHMVL
LEFVTAAGITLGMDELYK (SEQ ID 34)

1H8

MSKGEELFTGVVPILVELDGDVNGHKFSVSGEGEGDATYGKLTLKFICTTGKLRVPWPTLVTTLTYGVQCFSRYPDHMKQHDFFKSAMPECYVQERTIFYKDDGNYKTR
AEVKFEGDTLVNRIELKGIDFKEDGNILGHKLEYNYNSHIVYITGDKPKNGIKANFKIRHNIEDGSVQLADHYQLNTPIGDGPVLLPDNHYLSYQSALSKDPNEKRDHMVLL
EFVTAAGITLGMDELYK (SEQ ID 35)

2A3

CONTINUED FROM FIG. 7

MSKGEELFGGVIPVLVELEGDVNGQKFSVSGEGEGEGRPYEGFQTAKLKVTKGGPLPFAWDILSPQFCYGSKAYVKHPADIPDYLKLSFPEGFKWERMMNFEDGGVM
TVAQDSSLQDGEFIYKVKLRGTNFPSDGPVMQKKTMCWEASSERMYPEDGALKGEIKQRLKLKDGGHYDAEVKTTYKAKKPVQLPGAYIVGIKLDITSHNEDYTIVEQY
ERAEGRHSTGGMDELYK (SEQ ID 36)

2A8

MSKGEELFTGVVPVLVELDGDVNGQKFSVSGEGEGDATYGKLTLKFICTTGKLQVPWPTLVTTFGYGLQCFARYPDHMKQHDFFKSAMPEGYVQERTIFFEDDGNYKT
RAEVKFEGDTLVNRIELKGIDFKEDGNILGHKLECNFNSHNVYIMADKQKNGIKVNFKIRHNIEDGSVQLADHYQQNTPIGDGPVLLPDNHYLSYQSALSKDPNEKRNH
MVLLEFVTAAGITLGIDELYK (SEQ ID 37)

2B4

MSKGEENNMAVIKEFMRFKVRMEGSVNGHEFEIEGEGEGRPYEGTQTAKLKVTKGGPLPFAWDILSPQFMYGSKAYVKHPADIPDYLKLSFPEGFKWERMMNLEDG
GVVTVTQDSSLQDGEFINKVKLRGTNFPSDGPVMQKKTMSWEASSERMYPEDGALKGEIKMRLKLKDGGQYSAETKTTYKAKKPVQLPGAYIVGIKLDITSHNEDYTIV
EQYERAEGRHSTGGMDELYK (SEQ ID 38)

2C11

MSKGEELFTGVVPVLVELDGDVNGQKFSVSGEGEGDATYGKLTLKFICTTGKLRVPWPTLVTTLGYGLQCFSRYPDHMKQHDFFKSAMPESYVQERTIFFKDDGNYKTR
AEVKFEGDTLVNRIELKGIDFKEDGNILGHKLEYNFNSHNVYIMADKQKNGIKVNFKIRHNIEDGSVQLTDHYQQNTPIGDGPVLLPDNHYLSTQSTLSKDPNEKRDHMV
LLEFVTAAGITLGMDELYK (SEQ ID 39)

2C3

MSKGEELFTGVVPLLELDGDVNGHKFSVSGEGEGDATYGKLTLKFICTTGKLPVPWPTLVTTFSHGVQYFSRYPDHMKQHDFFKSAMPEGYVQERTIFFKDDGNYKTR
AEVKFEGDTLVNRIELKGIDFKEDGNILGHKLEYSYNSHNVYIMGDKPKNGIKVNFKIRHNIKDGGVQLADHYQQNTPIGDGPVLLPDNHYLSTQSALSKDPNEKRDHM
VLLEFVTAAGITHGMDELYK (SEQ ID 40)

2F9

CONTINUED FROM FIG. 7

MSKGEELFTGVVPILVELDGDVNGHKFSVSGEGEGDATYGKLTLKFICTTGKLQVPWPTLVTTLGYGLQCFARYPDHMKQHDFFKSAMPEGYVQERTIFFKDDGNYKTR
AEVIFEGDTLVNRIELKGIDFKEDGNILGHKMEYNYNSHNVYIMADKQKDGIKVNFKIRHNIEDGGVQLADHYQLNTPIGDGPVLLPDNHYLSYQSALSKDPNEKRDHM
VLLEFVTAAGITLGMDELYK (SEQ ID 41)

2G5

MSKGEELFTGVVPILVELDGDVNGHKFSVSGEGEGDATYGKLTLKFICTTGKLPVPWPTLVTTLGYGLQCFARYPDHMKQHDFFKSAMPEGYVQERTIFYKDDGNYKTR
AEVKFEGDTLVNRIELKGIDFKEDGNILGHKLEYNAISDIVYITADKQKNGIKANFKARHNIKDGSVQLADHYQQNTPIGDGPVLLPDNHYLSYQSALSKDPNEKRDHMVL
LEFVTAAGITLGMDELYK (SEQ ID 42)

2G8

MSKGEELFTGVVPVLVELDGDVNGHKFSVSGEGEGDATYGKLTLKFICTTGKLPVPWPTLVTTLYGVQCFSRYPDHMKQHDFFKSAMPEGYVQERTIFFKDDGNYKTR
AEVKFEGDTLVNRIELKGIDFKEDGNILGHKLEYNAISDIVYITADKQKNGIKANFKIRHNIEDGGVQLADHYQQNTPIGDGPVLLPDNHYLSTQSALSKDPNEKRDHMVL
LEFVTAAGITLGMDELYK (SEQ ID 43)

E1

MSKGEELFTGVVPILVELDGDVNGHKFSVSGEGEGDATYGKLTLKLICTTGKLRVPWPTLVTTFSYGVQCFSRYPDHMKQHDFFKSAMPEGYVQERTIFYKDDGNYKTR
AEVKFEGDTLVNRIELKGIDFKEDGNILGHKLEYNAISDIVYITADKQKNGIKANFKIRHNIEDGSVQLADHYQQNTPIGDGPVQLPDNHYLSYQSALSKDPNEKRDHMVL
LEFVTAAGITLGMDELYK (SEQ ID 44)

E3

MSKGEELFTGVVPILVELDSDVNGHKFSVSGEGEGDATYGKLTLKLICTTGKLRVPWPTLVTTFSYGVQCFSRYPDHMKQHDFFKSAMPEGYVQERTIFYKDDGNYKTR
AEVKFEGDTLVNRIELKGIDFKEDGNILGHKLEYNAISDIVYITADKQKNGIKANFKIRHNIEDGSVQLADHYQQNTPIGDGPVQLPDNHYLSYQSALSKDPNEKRDHMVL
LEFVTAAGITLGMDELYK (SEQ ID 45)

FLUORESCENT PROTEIN MOLECULES

This application claims benefit under 35 USC §119(e) of U.S. Provisional patent Application Ser. No. 61/201,034 filed Dec. 5, 2008.

FIELD OF THE INVENTION

The present invention relates to novel fluorescent proteins and to methods of making these proteins and the uses thereof.

BACKGROUND OF THE INVENTION

Fluorescent proteins such as green fluorescent protein (GFP) and Red fluorescent protein (RFP) are valuable tools for biological and biochemical research. For example GFP has been used to analyze bacterial gene expression during infection, to visualize tumor cell behavior during metastasis and to monitor GFP fusion proteins in gene therapy studies. Fluorescent proteins are also useful in high-throughput screening in drug discovery. Red fluorescent protein such as that produced by the coral Discosoma (DsRed) is also potentially useful as a fluorescent reporter protein or as a fusion tag.

There are a variety of known fluorescent proteins that can be used for various biological and biochemical studies (Griesbeck, O., Baird, G. S., Campbell, R. R., Zacharias, D. A., and Tsien, R. Y., (2001) Reducing the environmental sensitivity of yellow fluorescent protein, Mechanism and applications. *J. Biol. Chem.* 276, 29188-29194; Nagai, T. et al. (2002) A variant of yellow fluorescent protein with fast and efficient maturation for cell-biological applications. *Nat. Biotechnol.* 20, 87-90; Zapata-hommer, O. and Griesbeck, O. (2003) Efficiently folding and circularly permuted variants of the sapphire mutant of GFP. *BMC Biotechnol.* 3, 5 Rizzo, M. A., Springer, G. H., Granada, B., and Piston, D. W., (2004) An improved cyan fluorescent protein variant useful FRET. *Nat. Biotechnol.* 22, 445-449; Shaner, N. C., Campbell, R. E., Steinbach, P. A., Giepmans, B. N. G., Palmer, A. E. and Tsien, R. Y. (2004) Improved monomeric red, orange and yellow fluorescent proteins derived from Discosoma sp. red fluorescent protein. *Nat. Biotechnol.* 22, 1567-1572; Nguyen, A. W. and Daugherty, P. S. (2005) Evolutionary optimization of fluorescent proteins for intracellular FRET. *Nat. Biotechnol.* 23, 355-360.

There is still however a need to develop novel fluorescent proteins with different characteristics as experimental and clinical tools. Fluorescent proteins which emit at different wavelengths would be useful for the simultaneous detection of various biochemical parameters.

SUMMARY OF THE INVENTION

The present invention provides novel DNA and proteins of fluorescent proteins, method of making these proteins and uses of the fluorescent proteins. These proteins have excitation and emission spectra different than fluorescent proteins in the prior art. Visibly distinct colors and/or increased quantum yields of these proteins provides useful products for biochemical research including differential gene expression and protein localization.

BRIEF DESCRIPTION OF THE DRAWINGS

FIG. 3 is an illustration of on-chip assembly monitoring method. Detection oligos are mixed with ligator OligoMix. Once the full DNA is assembled on the chip, detection oligos can hybridize to the primer region, producing a fluorescent signal that can then be detected at the designated spot.

FIG. 4 are chip images and fluorescence intensities of detection oligos hybridized on the assembled monitor DNAs. The chip images were acquired using an Axon Genpix 400B scanner equipped with 532 and 635 nm excitation lasers. The intensities in the curve were obtained from the original images at 500 PMT. All images on the top were proportionally amplified using ArrayPro software to make 4-piece signal clearer.

FIGS. 5A and 5B are sequence listings of the DNA sequences of 5 novel fluorescent protein molecules.

FIG. 6 is sequence listings of the protein sequences of 5 novel fluorescent protein molecules.

FIG. 7 is an alignment of the protein sequences of various known and novel fluorescent protein molecules.

DEFINITIONS

Figure 1:
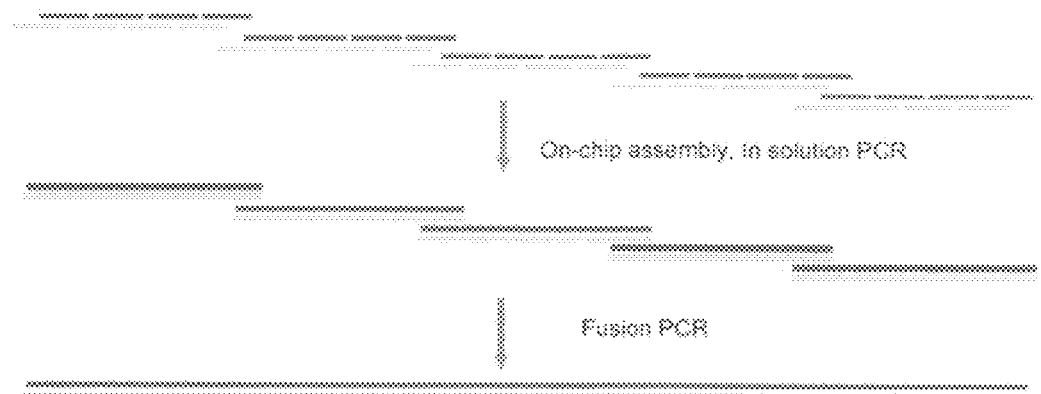
FIG. 1 is a schematic illustration of fluorescent protein coding DNA synthesis method. Five intermediate fragments were parallel assembled on the capture chip using ligator oligos synthesized on the ligator chip.

The following terms are intended to have the following general meaning as they are used herein:

The term "DNA fragment" means a DNA sequence which is partial or full length DNA to be assembled.

The term "full length DNA" means the complete sequence of the target DNA to be synthesized.

The term "capture array" means a surface containing more than one capture oligos.

The term "substrate" and "surface", and "solid support" are used interchangeably to refer to any material that is suitable for derivatization with a functional group and for nucleic acid synthesis.

The term "nucleotide" refers to a compound comprised of a base linked to a pentose sugar through a glycosidic bond and a phosphate group at the 5'-position of the sugar. Natural nucleotides contain bases which are adenine (A), cytidine (C), guanine (G), thymine (T), and uridine (U).

The term "modified nucleotide" refers to a compound which contains chemical moieties that is different from or additional to those of natural nucleotides.

The term "linker" refers to an anchoring group that serves to anchor or tether a molecule to a solid support during solid phase synthesis.

The term "spacer" refers to a chemical group connected to a linker or an anchor moiety that is used to in between the linker and the immobilized nucleic acids or oligonucleotides and as a site for initiating synthesis of a polymer chain. Examples of spacer include, but are not limited to, ethyleneglycol polymer, alkyl, molecules containing branch side chains, dendrimers, oligonucleotides, peptides, peptditomimetics. Spacer molecules are sometimes terminated with hydroxyl or amino groups for synthesis of oligonucleotides or immobilization of nucleic acid sequences.

The term "3'-5' synthesis" refers to the addition of a 3'-phosphoramidite nucleotide to the 5'-OH end of a polynucleotide chain; 3'-5' synthesis is commonly used for oligonucleotide synthesis.

The term "5'-3'synthesis" refers to the addition of a 5'-phosphoramidite nucleotide to the 3'-OH end of a polynucleotide chain. The 5'-3'synthesis is also termed reverse synthesis.

The term "failure sequence" refers to the oligos obtained from a synthesis whose sequences are incorrect according to what are designed. The errors in failure sequences include deletion, insertion, and substitution of nucleotides, and the truncation of oligonucleotides.

The term "dye" refers to a molecule, compound, or substance that can provide an optically detectable signal (e.g., fluorescent, luminescent, calorimetric, topological, etc). For example, dyes include fluorescent molecules that can be associated with nucleic acid molecules.

The term "labeling" refers to a modification to nucleic acid and oligonucleotides which provides signals for the detection of the sequences containing the label. The detectable labels include any composition capable of generating signals detectable by spectroscopic, photochemical, biochemical, immunochemical, electrical, optical, topological, or chemical means.

The term "detection tag" is a moiety that can be attached to nucleic acid and oligos to produce detection signal intramolecularly or serve as a means for generation of detection signals. A well-known example is biotin as a detection tag and its binding to strepavidin that is modified with a moiety capable of generating detection signals. The detectable tags include any composition detectable by spectroscopic, photochemical, biochemical, immunochemical, electrical, optical, topological, or chemical means.

The term "oligonucleotide" refers to a molecule comprised of two or more deoxyribonucleotides and/or ribonucleotides joining through phosphodiester bonds; the term "oligonucleotide" is not limited to nucleotides of natural types but may include those containing chemical modifications at the moieties of base, sugar, and/or backbone. An oligonucleotide sequence is written in 5'- to 3' direction by convention unless otherwise defined.

The terms "nucleic acid" and "nucleic acid sequence" are used interchangeably to refer to a deoxyribonucleotide or ribonucleotide polymer or oligomer, in either double or single stranded form, and unless otherwise noted would encompass known analogues of naturally occurring nucleotides that can function in the same or similar manner thereto.

The term "primer" refers to a polynucleotide, which is capable of annealing to a complementary template nucleic acid and serving as a point of initiation for template-directed nucleic acid synthesis, such as a polynucleotide amplification reaction. A primer need not reflect the exact sequence of the template but must be sufficiently complementary to hybridize with a template.

The term "duplex" and "double strand" are used interchangeably to refer to at least partial or complete alignment of two strands of oligonucleotides or nucleic acids in an antiparallel orientation with regard to the 5'-terminus of one strand annealed to the 3'-terminus of the other strand.

The terms "hybridization" and "binding" in the context of the association of strands of nucleic acid or oligonucleotides are used interchangeably. The term defines reactions which are intended to bring two strands of sequences to form duplexes or at least partial duplexes through base pair formation. Typical hybridization leads to formation of antiparallel duplexes with regard to the 5'-end of each strand. Natural nucleic acid forms base pairs between A and T and between G and T in DNA or G and U in RNA. These are complementary base pairs.

The term "anneal" refers to specific interaction between strands of nucleotides wherein the strands bind to one another substantially based on complementarity between the strands as determined by Watson-Crick base pairing.

The term "array" and "microarray" are used interchangeably to refer to a multiplicity of different sites sequences attached to one or more solid supports. The term array can refer to the entire collection of oligonucleotides on the supports (s) or to a subset thereof. The sequences immobilized on the surface in an array through linker and/or spacer are probes or capture probes.

The term "capture probe" refers to an oligonucleotide capable of binding to a target nucleic acid of complementary sequence through one or more types of chemical bonding usually though complementary base-pairing through hydrogen bond formation. The capture probe is designed to be sufficiently complementary to a target oligonucleotide sequence under selected hybridization conditions. As used herein a capture probe may include natural ribonucleotides or deoxyribonucleotides nucleotides such as adenine, guanine, cytosine and thymidine or modified residues, such as those methylated nucleobases, 7-deazaguanosine or inosine, 5'-phosphate, thioate internucleotide linkages, or other modification groups. The nucleotide bases in a capture probe may also be linked by phosphodiester bonds or other bonds (e. g., phosphorothioate) as long as the alternative linkage does not interfere with hybridization. Capture probes may contain or completely are made of locked nucleic acids (LNAs), and/or other modified nucleotide residues, or peptide nucleic acids (PNAs) in which the constituent bases are joined by peptide linkages. The capture probe may contain one or more linkers and/or one or more spacers, and the capture probe may be immobilized through either its 5'- or 3'-end linked to the spacer or linker.

The term "ligated sequence" refers to a sequence which is formed by the ligation of one or more oligonucleotides. The ligation oligonucleotides may include capture probe that has been extended by ligation of one or more oligonucleotides. The term includes ligated oligonucleotides of chain extension whether the ligation performed sequentially or simultaneously by one or more ligator oligonucleotides.

The term "ligation", "ligate", or "ligating" is used in the context that refers the reaction joining two nucleic acid sequences through covalent bonds. Typically, ligation requires a template and hybridization of two sequences with the template strand with the 5'-terminus phosphate group of one hybridizing strand next to the 3'-OH of the other hybridizing strand and formation of a phosphodiester bond by the action of ligase enzymes. Ligation occurs between two duplexes of cohesive ends which are complementary to each other or of blunt ends. Ligation occurs between two single strands which are DNA and/or RNA. The term "ligation" broadly refers to reactions involving gap filling and ligation steps. In the context of the present invention the term "ligation", "ligate", or "ligating" is intended to encompass gap filling which is to add nucleotides to the sequences at the ligation site to make ligatable ends between the two hybridizing sequences aligned with the same template sequence. In the context of the present invention the term "ligation", "ligate", or "ligating" is also intended to encompass other methods of covalently linking such sequences, for example, by chemical means.

The term "ligase" refers to an enzyme used to catalyze ligation reactions. DNA ligase covalently link DNA strands, RNA ligase covalently link RNA strands, some ligase enzymes also catalyze the covalent linkage of RNA to RNA and/or RNA to DNA molecules of single stranded or duplex forms.

The term "ligator" is used to refer to oligonucleotides that can hybridize to form hybridizing duplex containing nicking and/or gapping sites. Ligator oligos as used in the present invention contain either 5'-P and/or 3'-OH for ligation.

The term "template strand" and "template sequence" are used interchangeably in the context of ligation to refer to the sequence that is at least in part in separate regions, complementary to two sequences. The hybridization of the three strands allows ligation in the form of duplex formation among the three sequences.

DETAILED DESCRIPTION OF THE INVENTION

The present invention provides novel DNA and proteins of fluorescent proteins, method of making these proteins and uses of the fluorescent proteins. The DNA sequences of the novel proteins of the present invention can be made according to the procedures described in WO07040592. Generally, synthesis of the DNA sequences of the novel fluorescent proteins are made by synthesized DNA fragments that are hybridized and ligated to one another on a microarray. Capture probes are placed onto a solid supports. The placement of the capture probe on the solid support can be accomplished by "spotting" the pre-synthesized capture probes onto the support; alternatively capture probes can be placed onto the solid support by de novo synthesis of the capture probe on the solid support. The capture probe can be attached to the solid support through immobilization of linkers and/or spacers which are well known by those skilled in the art. The orientation of the capture probes may be in the direction of either the 3'→5' or 5'→3', and in the case where the capture probe is synthesized de novo, the appropriate selection of linkers and/or spacers and/or nucleotides to achieve the desired orientation is required. Once the capture probes are secured to the solid support, target nucleic acid sequences of single-stranded or duplex are added to the capture probes and hybridized to the capture probes under specific hybridization conditions. In some or all cases, upon hybridization, a portion of the target sequences forms duplex with the capture probes but a region of the target sequences is single-stranded. After the hybridization of the target sequences and capture probes, ligation oligos (ligators) that are specific to the portion of the target sequences which is adjacent to the capture probe sequence are added and hybridized to the single-stranded region of the target sequences in the capture probe-target sequence duplexes. The design of the capture probe and ligator oligo provides that after the above steps are completed that both sequences are hybridized to the same target sequence and one end of the capture oligo and one end of the ligator are in close proximity such that ligation of the capture probe and ligator oligo can be effectuated by the addition of ligase under appropriate conditions. The ligation of capture probe and ligator oligo extends the chain length of the original sequences and the resultant product is called ligated nucleic acid sequence.

Another target/ligator as an oligo mixture, hybridization of these oligos to the capture probes in the initial cycle and to the single-stranded region of the surface sequences in repetition cycles can be repeated multiple times or can be accomplished in a single step. The addition of the oligo mixture may be serial, simultaneous, or a combination thereof. For example, after the initial hybridization of the oligo mixture to the capture probe, the stepwise addition of oligo mixture for hybridization and ligation steps result in nucleic acid polymer of extended chain length. Alternatively, the stepwise addition of oligo mixture for hybridization may be repeated more than once, and the ligation step is then performed. These reactions result in nucleic acid polymer of extended chain length. Also alternatively, the steps of addition of oligo mixture for hybridization and ligation can be performed in combination and the reaction result in nucleic acid polymer of extended chain length A useful property of the ligated sequences is the presence of priming sites which may be specific sequences or common in several or all ligated sequences. Examples of these priming regions include promoter sequence for transcription and universal primers for PCR. Therefore, the ligated sequences can be amplified for various applications. After hybridizing and ligation reactions, PCR reactions are performed separately using the corresponding complementary primers using the oligo mixture. This results in amplification in each PCR reaction a specific subset of oligo mixture.

Trinucleotide codons are often used as a unit for randomization in the generation of protein or peptide coding sequences. There are 61 codons for expression of 20 natural amino acid and there are 20 preferred codons for protein expression in *E. coli*. The methods of the present invention can be used to synthesize a library of protein sequences. The corresponding DNA sequences are written as pseudo-sequences using pseudo-codons. The group number corresponds to a defined mixture of nucleotides. Each pseudo-codon represents several coding sequences and several amino acid residues. Each pseudo-sequence represents a number of oligo sequences and several peptide sequences. The combinations of nucleotide mixtures (groups) and composition of the pseudo-codons may vary from time to time according to the requirement of the protein sequence design and the synthesis. The selection of five pseudo-codons for synthesis of the DNA sequences in a region coding for seven amino acids results in 78,125 pseudo sequences containing predetermined pseudocodons, which represent 62,748,517 individual sequences of natural nucleotides and grouped by the pseudo-codon arrangement in a sequence. The prescribed method of randomization in the synthesis is referred as restricted randomization (rRAM). The design of different combinations of pseudo-codons for synthesis of an array of oligo mixtures determines the generation of large sequence libraries.

The present invention demonstrates long DNA synthesis by hybridization and ligation of a set of oligos. The number of oligos may be determined according to the length of the gene to be synthesized. The synthesis may complete the full length of the gene, or alternatively several fragments of the gene may first be assembled and these fragments can then assembled to generate the full length gene. The lengths of oligos are generally 6-100 residues, preferably 15-80 residues and more preferably 25-70 residues. Duplexes may be directly synthesized or produced as PCR products, which may need to be treated with restriction enzymes for removal of primer sequences which are not part of the genes to be assembled. The strategies of long DNA sequences may include:
  (a) The genes to be synthesized may be either single or double strands.
  (b) An oligo set may contain sequences that are designed as partially overlapping duplexes. Hybridization and ligation to join these sequences produce long DNA sequence.
  (c) Two sets of oligo duplexes may be designed as partially overlapping duplexes. The end of these duplexes may be blunt or contains overhanging sequences. Hybridization and ligation to join these sequences produces long DNA sequence.

(d) An oligo set contains sequences that are designed as partial overlapping duplexes. DNA amplification reaction extends the overlapping duplexes into a full-length duplex.

The methods of the present invention can be used for the synthesis of DNA for generation of protein libraries containing more than ten different protein sequences and potentially up to $10^{16}$ different proteins. The ligated DNA sequences obtained from on-surface ligation may be directly cloned or cloned after amplification into an expression vector. In case of amplification, the primer regions can be removed from the amplified products by restriction enzymes. Alternatively, primers containing RNA residues at the designed cleavage site may be used for primer region removal. Long DNA synthesis may use ligated oligos and primers containing RNA residues. The ligated DNA sequences are not limited to two and multiple fragments of ligated DNA or any other DNA duplexes of the suitable sequences may be used to generate longer DNA sequences by having ligated sequences in single strands or duplexes and primers containing RNA residues at the position of cleavage, and performing amplification reactions; using RNase enzyme to cleave the RNA bonds; using single-strand DNA nuclease to digest the dangling ends formed after removal of the primers; performing overlapping PCR to produce long DNA. Alternatively, a restriction enzyme cleavage site may be engineered for removal of the primer sequence after amplification. Performing overlapping PCR produces long DNA.

The methods of the present invention include the synthesis, hybridization, and ligation of oligos performed on spatially separated surfaces. The present invention includes ligation reactions carried out in parallel on surface that has a density from at least nine sites per mm$^2$ to about $2.0 \times 10^{11}$ sites per mm$^2$. In a preferred embodiment of the present invention, the reactions are performed using a three-dimensional microfluidic device (Zhou and Gulari, USP Application 20030118486; Zhou et al. 2004).

The present invention also utilizes three dimensional microfluidic microchip technologies to enable the manufacture of long segments of nucleic acids inexpensively and efficiently. Such microfluidic microchip devices and synthesis methods are described in US Patent Publication No. 20020012616, US Patent Publication No. 20030118486 and U.S. Pat. No. 6,426,184 which are incorporated by reference. However, the surface and surface immobilized capture probes used for making long DNA sequences are not limited to those produced by the synthesis methods described herein, and these may be obtained by spotting of pre-synthesized oligos.

Any desired DNA sequence can be produced by the methods described above. In the Examples that follow the method of producing designed DNA was used to produce various fluorescent proteins that have DNA and protein sequences different from those described in the prior art. These proteins also have different emission and excitation spectra as well as in some cases increased quantum yields. The DNA sequences of the present invention include variants of fluorescent proteins which have at least 90% identity with the DNA sequences shown in SEQ ID NOs. 1, 2, 3, 4 or 5. The DNA sequences of the present invention include variants of fluorescent proteins which have at least 95% identity with the DNA sequences shown in SEQ ID NOs. 1, 2, 3, 4 or 5. The DNA sequences of the present invention include variants of fluorescent proteins which have at least 99% identity with the DNA sequences shown in SEQ ID NO. 1, 2, 3, 4 or 5. In preferred embodiments of the DNA sequences of the present invention the variants of fluorescent proteins which have at least 90%, 95% or 99% identity with the DNA sequences shown in SEQ ID NOs. 1, 2, 3, 4 or 5 will when expressed produce proteins with emission and excitation spectra similar or identical to that of the sequences shown in SEQ ID NOs. 1, 2, 3, 4 or 5. The protein sequences of the present invention include variants of fluorescent proteins which have at least 90% identity with the protein sequences shown in SEQ ID NOs. 6, 7, 8, 9 or 10. The protein sequences of the present invention include variants of fluorescent proteins which have at least 95% identity with protein DNA sequences shown in SEQ ID NOs. 6, 7, 8, 9 or 10 6, 7, 8, 9 or 10. The protein sequences of the present invention include variants of fluorescent proteins which have at least 99% identity with the protein sequences shown in SEQ ID NOs. 6, 7, 8, 9 or 10. In preferred embodiments of the DNA sequences of the present invention the variants of fluorescent proteins which have at least 90%, 95% or 99% identity with the DNA sequences shown in SEQ ID NOs. 6, 7, 8, 9 or 10 will when expressed produce proteins with emission and excitation spectra similar or identical to that of the sequences shown in SEQ ID NOs. 6, 7, 8, 9 or 10.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, chemistry or related fields are intended to be within the scope of the following claims.

EXAMPLES

The following examples are included to demonstrate embodiments of the invention. It should be appreciated by those of skill in the art that the techniques disclosed in the examples are representative techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Target Fluorescent Protein DNA Sequences

Seventeen fluorescent proteins were obtained from literature or Entrez database[i,ii,iii,iv,v,vi,vii]. These proteins are primarily variants of two families: GFP with 238 amino acids, and RFP with 235 amino acids. These proteins have been reported to have relative high brightness.

The DNA sequences of the 17 collected proteins were reverse-translated using the highest-frequency *E. coli.* codons[viii] to give 17 DNA constructs as synthesis targets. The resultant DNA sequences were then optimized by using second- or third-frequency *E. coli.* codons to eliminate: 1) long stretches of repetitive fragments, as these sequences will result in non-specific annealing. 2) GC-rich followed by AT-rich sequences which could potentially result in early termination of transcription,[ix] and 3) restriction enzyme recognition sites used in the common primers. In total, twelve 714-bp DNA sequences (from 238-aa FP) and five 705-bp DNA sequences (from 235-aa FP) were generated for synthesis. An EGFP DNA sequence (Genbank ID: AAK15492) was included as a control.

All sequences were flanked with AAGGATCC and CTCGAGAA at the 5' and 3' end, respectively. The underlined sequences represent BamHI and XhoI restriction enzyme recognition sites and they facilitate cloning the synthetic FP DNA into pET-20b expression vectors (Novagen, Madison Wis.).

Example 2

Design of Oligonucleotide Sequences for Synthesis of DNA Constructs

The SeqZego program developed in house was applied to design the oligos as shown in FIG. 1. First each FP coding DNA sequence was divided into five approximately 169-bp fragments with adjacent fragments overlapping by approximately 30 bp. Two common primers containing BbsI recognition sites, ACGCTCTGAAGACCC and CTGTCTTCTATCTCG, were incorporated such that they flanked the 5' end and the 3' end of each fragment, respectively. Each fragment was constructed of four plus strand oligos and four minus strand oligos such that, upon annealing, the oligos in the same strand were consecutively connected while the neighboring oligos of the plus and minus strands were partially overlapping (cohesive stacking). The lengths of all oligos varied between 40 and 50-mers to minimize the $T_m$ difference. Each oligo of ligators contained the primers CACAGGAGTCCTCAC and CTAGCGACTCCTTGG at the 5' and 3' end, respectively (underlined sequences are MlyI recognition sites).

Thus, to synthesize eighteen FPs, a total of 90 fragments need to be assembled with 540 ligators and 180 capture probes.

Example 3

Oligonucleotide Synthesis on the Ligator and Capture Chips

The ligator oligos and capture oligos were synthesized on a ligator chip and capture chip, respectively. The microchip synthesis was based on phosphoramidite chemistry, using photogenerated acids (PGAs) to deprotect the DMT group. Light irradiation from a programmable digital light projector induced the photogenerated acid precursor (PGAP) to generate the acid which removes the DMT yielding 5'-OH groups for coupling. A computer program controls the light irradiation sites at each cycle based on the designed DNA sequences.

After the synthesis of the last nucleotide for each of the oligos, all capture oligos on the capture chip were coupled with a 5'-phosphate group for ligation reactions using a phosphorylating agent. All ligators on the ligator chip were coupled with fluorescein phosphoramidite (Glen Research, Sterling Va.) for the quality assessment of the synthesis.[x]

Example 4

Ligator Oligo Preparation

The fluorescent image of the directly labeled ligator oligos was acquired by an Axon laser scanner (GenePix 4000B), and signal intensities were obtained using ArrayPro (Media Cybernetics, Bethesda Md.). The ligator oligos were cleaved from ligator chip by circulating the chip with 200 ul fresh ammonia at 50° C. for 1 hour. After cleavage the chip was scanned again to evaluate the cleavage efficiency.

The cleaved solution was speed vacuumed to about 50 ul, and the ligator oligos were recovered by phenol:chloroform: isoamyl alcohol extraction and ethanol precipitation.[xi] The final pellets were dissolved into 50 ul dd $H_2O$. 10 pmol ligators were obtained based on the UV absorption at 260 nm measured using a 3100 Nanodrop (Nanodrop).

To amplify the ligator oligos, a 400 ul PCR reaction was prepared which contained 40 ul 10×buffer (Stratagene LaJolla Calif.), 40 ul of primers (GCAAGTCACAGGAGTCCTCAC and CACTGTCCAAGGAGTCGC, 10 uM), 8 ul 10 mM dNTP(Invitrogen), 4 ul DMSO, 4 ul oligo solution, 8 uL PfuUltra polymerase (Stratagene, LaJolla Calif.) and dd $H_2O$. The reaction mixture was denatured for 1 min at 94° C., followed by 24 cycles of 30 s at 94° C. for denaturation, 60 s at 56° C. for annealing, and 30 s at 72° C. for extension.

The PCR products were purified with QIAGEN nucleotide removal kit. DNA was eluted into 50 ul EB solution (10 mM Tris, pH 8.0). To remove the primers at both the 5' and 3' ends, 5 ul MlyI restriction enzyme (New England Biolabs, Ipswich Mass.), 10 ul NEBuffer IV, 1 ul BSA, and 34 ul dd$H_2O$ were added to elution solution. The digestion was performed at 37° C. for 3 hours. A YM3 column was applied to reduce the salt and water in the digestion product. Finally a volume of 100 ul ligator oligo was recovered (1.1 uM concentration based on the UV absorption at 260 nm measured using a 3100 Nanodrop).

Example 5

Figure 2:
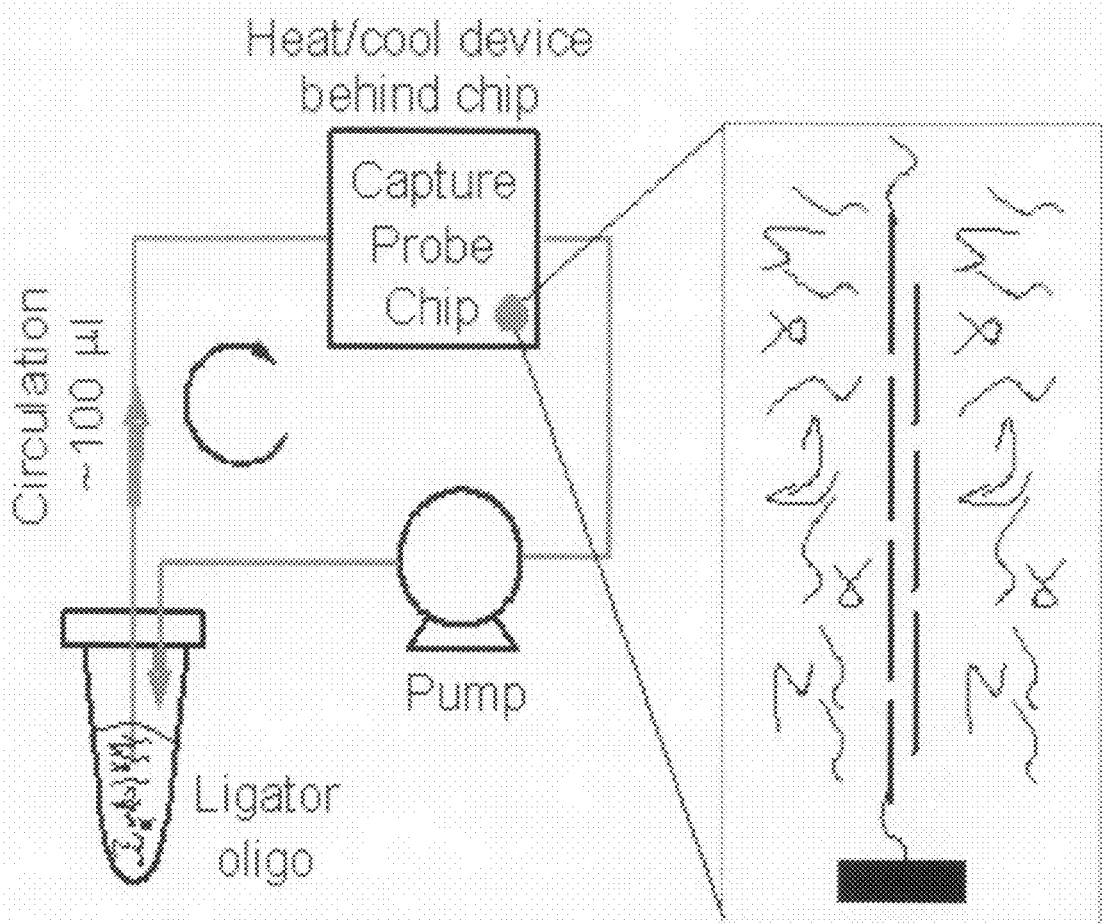
FIG. 2 is a schematic illustration of a temperature-controlled apparatus for on-chip annealing-wash-ligation reactions. The heat/cool device can control the temperature of chip. The ligator oligo solution is circulated using a microperistaltic pump and the flow rate is adjustable (20-2,000 ul/min).

Fragment Synthesis on the Capture Chip 100 ul 1.1 uM ligator oligos as an OligoMix was mixed with 100 ul 2×hybridization buffer to give a final solution with 0.9 M NaCl, 60 mM $NaH_2PO_4$, and 25% formamide, and pH 6.8. The solution was heated to 95° C. for 10 min, and then quenched on ice for 5 min. The solution was circulated through the capture chip at a rate of 100 ul/min with the equipment shown in FIG. 2. During annealing, the circulation tubing of the OligoMix solution was maintained at 95° C. and the capture chip was maintained at 50° C.

Annealing continued for 7 h and the capture chip was then washed with 0.1×SSPE buffer at room temperature, followed by 0.1×SSPE buffer at 35° C., 40° C., and 45° C., each time for 10 min, respectively. After washing, the chip was bathed in Taq ligation buffer (NEB) at room temperature for 10 min. Then 5 uL Taq DNA ligase (NEB, Ipswich Mass.) 40 unit/ul was added. The ligation was performed at 50° C. overnight. After the ligation, the chip was stripped with strip buffer (5 mM MES, 0.3 mM EDTA, 50% formamide, pH 6.8) at 40° C. for 10 minute, and then washed with $H_2O$ to remove residual salt.

Example 6

In Situ Monitoring of Fragment Synthesis

Five monitor DNA sequences were parallel assembled on the capture chip in situ to monitor the fragment synthesis process. These DNA sequences were divided using SeqZego program into different pieces of construction oligos as shown in FIG. 4. All 3' end oligos were synthesized on the capture chip as capture oligos, and all other oligos were subjected to the same procedures as FP DNA ligator oligos, i.e., synthesized on the ligator chip, cleaved, amplified by PCR, digested with enzyme to remove primers. During the annealing, 1 nM Cy5 labeled detection oligos were mixed with ligator Oligo-Mix.

During the annealing process, the capture chip was scanned every hour. Only after pseudo duplexes formed could detection oligos hybridize to their designated positions. The resulting appearance of a fluorescent signal indicated the success of annealing. In 6 hours the fluorescence intensity reached a plateau. The annealing was stopped after 7 hours. FIG. 4 shows the chip images and detection oligo intensities.

Example 7

Full FP DNA Synthesis

The assembled DNA fragments were cleaved from the capture chip with 200 ul fresh ammonia, which was speed vacuumed to about 50 ul. Fragment amplification was carried out in 100 ul PCR reaction containing 1 ul assembled fragment solution, 2 uM of primers (TGGTGTACGCTCTGAA-GACCC and TGCGGCCGAGATAGAAGACAG), 0.2 mM each dNTP, 5 unit PfuUltra polymerase in 1×buffer (Stratagene, LaJolla Calif.). The reaction mixture was denatured for 1 min at 94° C., followed by 24 cycles of 30 s at 94° C. for denaturation, 60 s at 56° C. for annealing, and 30 s at 72° C. for extension.

The PCR products were purified with QIAGEN PCR kit. DNA was eluted into 50 ul EB solution (10 mM Tris, pH 8.0). 5 ul BbsI restriction enzyme (New England Biolabs, Ipswich Mass.), was incubated with 10 ul NEBuffer IV, 1 ul BSA, 34 ul ddH$_2$O, and 50 ul DNA at 37° C. for 3 hours to remove primers containing BbsI recognition sites. A YM3 column was applied to reduce the salt and water in the digestion product.

A two-step fusion PCR reaction was applied to assemble full DNA. First, a 15-cycle extension reaction without primer was carried out. The composition of the extension reaction was: 5 unit PfuUltra polymerase (Stratagene, LaJolla Calif.) and 0.2 mM each dNTP for 100 ul PCR reaction. About 1 ng of DNA template was used. PCR started at 94° C. for 1 min, and was followed by 15 cycles of 30 s at 94° C. for denaturation, 60 s at 55° C. for annealing, and 60 s at 72° C. for extension. Second, a 24-cycle of amplification with 2 um each primer was performed. The polymerase and dNTP were the same as the first step, 1 ul fusion PCR product was used as the template. PCR started at 94° C. for 1 min, followed by 24 cycles of 30 s at 94° C. for denaturation, 60 s at 50° C. for annealing, and 60 s at 72° C. for extension.

Example 8

Fluorescent Protein Expression

The PCR products derived in Example 7 were cloned in an appropriate expression vector and several of those clones demonstrating expression of fluorescent proteins were selected for DNA sequencing. Five of the sequences are listed in FIGS. 5A and 5B. The protein sequence for each of these DNA sequences is listed in FIG. 6. Once sequenced the proteins expressed by these clones were purified using a NI-chelate column. Fluorescent proteins were eluted with a 300 mM solution of imidazole.

Example 9

Fluorescent Protein Characterization

The proteins designated 2G2, 2B11, 1H10, E6 and 1H3 that were purified in Example 8 were subjected to various tests that characterize the proteins. UV absorption data for each of the novel fluorescent protein was performed on a HITACHI F-4500 with exciting slit 2.5 nm and emission 5 nm. The fluorescent protein sample concentration was 0.05 mg/mL for each.

| Protein | 2B11 | 2G2 | eGFP | H3 | H10 | E6 |
|---|---|---|---|---|---|---|
| UV$_{max}$ (nm) | 475 | 485 | 485 | 502 | 544 | 550 |
| UV$_{sec}$ (nm) | | | | 565 | 502 | 520 |

The emission spectra and quantum (QY) yield of each of the novel fluorescent proteins was determined:

| Protein | 2B11 | 2G2 | eGFP | 1H3 | 1H10 | 1E6 |
|---|---|---|---|---|---|---|
| excitation | 475 | 486 | 486 | 535 | 535 | 535 |
| emission | 507 | 509 | 511 | 570 | 555 | 565 |
| QY | 0.59 | 0.71 | 0.60 | 0.05 | 0.19 | 0.08 |

[i] Griesbeck, O., Baird, G. S., Campbell, R. R., Zacharias, D. A., and Tsien, R. Y., (2001) Reducing the environmental sensitivity of yellow fluorescent protein, Mechanism and applications. *J. Biol. Chem.* 276, 29188-29194

[ii] Nagai, T. et al. (2002) A variant of yellow fluorescent protein with fast and efficient maturation for cell-biological applications. *Nat. Biotechnol.* 20, 87-90

[iii] Zapata-hommer, O. and Griesbeck, O. (2003) Efficiently folding and circularly permuted variants of the sapphire mutant of GFP. *BMC Biotechnol.* 3, 5

[iv] Rizzo, M. A., Springer, G. H., Granada, B., and Piston, D. W., (2004) An improved cyan fluorescent protein variant useful FRET. *Nat. Biotechnol.* 22, 445-449

[v] Shaner, N. C., Campbell, R. E., Steinbach, P. A., Giepmans, B. N. G., Palmer, A. E. and Tsien, R. Y. (2004) Improved monomeric red, orange and yellow fluorescent proteins derived from Discosoma sp. red fluorescent protein. *Nat. Biotechnol.* 22, 1567-1572

[vi] Nguyen, A. W. and Daugherty, P. S. (2005) Evolutionary optimization of fluorescent proteins for intracellular FRET. *Nat. Biotechnol.* 23, 355-360

[vii] http://www.ncbi.nlm.nih.qov/sites/entrez?db=protein

[viii] http://www.kazusa.or.jp/codon/

[ix] Gustafsson, C., Govindarajan, S. and Minshull, J. (2004) Codon bias and heterologous protein expression. Trends in biotechnology 22, 346-353

[x] Tian, J., Gong, H., Sheng, N., Zhou, X., Gulari, E., Gao, X. and Church, G. (2004) Accurate multiplex gene synthesis from programmable DNA chips. *Nature* 432, 1050-1054

[xi] Zhou, X., Cai, S., Hong, A., Yu, P., Sheng, N., Srivannavit, O., Yong, Q., Muranjan, S., Rouilard, J. M., Xia, Y., Zhang, X., Xiang, Q., Ganesh, R., Zhu, Q., Makejko, A., Gulari, E. and Gao, X. (2004) Microfluidic PicoArray synthesis of oligodeoxynucleotides and simultaneously assembling of multiple DNA sequences. *Nucleic Acids Res.* 32, 5409-5417.

I claim:

1. An isolated nucleic acid sequence comprising SEQ ID NO:1.

\* \* \* \* \*

SEQUENCE LISTING

<160> NUMBER OF SEQ ID NOS: 45

<210> SEQ ID NO 1
<211> LENGTH: 714
<212> TYPE: DNA
<213> ORGANISM: Artificial Sequence
<220> FEATURE:
<223> OTHER INFORMATION: discosoma

<400> SEQUENCE: 1

| | | | | | |
|---|---|---|---|---|---|
| atgagcaaag | gcgaagaact | gttcaccggt | gtggtgccga | tcctggtgga | actggatggc | 60 |
| gatgtgaacg | gccagaagtt | cagcgtgagc | ggcgaaggcg | aaggcgatgc | gacctatggc | 120 |
| aaactgaccc | tgaagttcat | ctgcaccacc | ggcaaactgc | cggtgccgtg | gccgaccctg | 180 |
| gtgaccaccc | tgggctatgg | cctgcagtgc | ttcgcgcgct | atccggatca | tatgaaacag | 240 |
| catgatttct | tcaagagcgc | gatgccggaa | ggctatgtgc | aggaacgcac | catcttcttc | 300 |
| aaagatgatg | gcaactacaa | gacccgcgcg | gaagtgaaat | tcgaaggcga | taccctggtg | 360 |
| aaccgcatcg | aactgaaagg | catcgatttc | aaagaagatg | gcaacatcct | gggccataaa | 420 |
| ctggaataca | actataacag | ccataacgtg | tatatcaccg | cggataaaca | gaagaacggc | 480 |
| atcaaagcga | acttcaaaat | ccgccataac | atcgaagatg | gcagcgtgca | gctggcggat | 540 |
| cattatcagc | agaacacccc | gatcggcgat | ggcccggtgc | tgctgccgga | taaccattat | 600 |
| ctgagcaccc | agagcgcgct | gagcaaagat | ccgaacgaga | aacgcgatca | tatggtgctg | 660 |
| ctggaattcg | tgaccgcagc | gggcatcacc | catggcatgg | atgaactgta | caag | 714 |

<210> SEQ ID NO 2
<211> LENGTH: 714
<212> TYPE: DNA
<213> ORGANISM: Artificial Sequence
<220> FEATURE:
<223> OTHER INFORMATION: discosoma

<400> SEQUENCE: 2

| | | | | | |
|---|---|---|---|---|---|
| atgagcaaag | gcgaagaact | gttcaccggc | gtggtgccga | tcctggtgga | actggatggc | 60 |
| gatgtgaacg | gccataagtt | cagcgtgagc | ggcgaaggcg | aaggcgatgc | gacctatggc | 120 |
| aaactgaccc | tgaagttcat | ctgcaccacc | ggcaaacttc | ccgtgccctg | gcccacccts | 180 |
| gtgaccaccc | tgacctacgg | cgtgcagtgc | ttcagccgct | atccggatca | tatgaaacag | 240 |
| catgatttct | tcaagagcgc | gatgccggaa | ggctatgtgc | aggaacgcac | catcttctac | 300 |
| aaagatgatg | gcaactacaa | gacccgtgcg | gaagtgaagt | tcgaaggcga | taccctggtg | 360 |
| aaccgcatcg | aactgaaagg | catcgatttc | aaagaagatg | gcaacatcct | gggccataaa | 420 |
| atggaataca | acttcaacag | ccataacgtg | tatatcatgg | gcgataaacc | gaaaaacggc | 480 |
| atcaaagtga | acttcaaaat | ccgccataac | atcaaagatg | gcggcgtaca | gctggcggat | 540 |
| cattatcagc | tgaacactcc | gatcggcgat | ggcccagtga | tcctgccgga | taaccattat | 600 |
| ctgagcaccc | agagcgcgct | gagcaaagat | ccgaacgaga | aacgcgatca | tatggtgctg | 660 |
| ctggaattcg | tgaccgcagc | tcgcatcacc | catggcatgg | atgaactgta | caag | 714 |

<210> SEQ ID NO 3
<211> LENGTH: 705
<212> TYPE: DNA
<213> ORGANISM: Artificial Sequence
<220> FEATURE:
<223> OTHER INFORMATION: discosoma

<400> SEQUENCE: 3

```
atgagcaaag gcgaagaaga taacatggcg atcatcaaag agttcatgcg cttcaaagtg      60
cgcatggaag gcagcgtgaa cggccatgaa ttcgaaatcg aaggtgaagg tgaaggccgc     120
ccgtatgaag gcacccagac cgcgaaactg aaagtgacca aaggcggtcc gctgccgttc     180
gcgtgggata tcctgagccc gcagttctgc tatggcagca aagcgtatgt gaaacatccg     240
gcggatatcc cggattactt caaactgagc ttcccggaag cttcaaatg ggaacgcatg      300
atgaacttcg aagatggcgg tgtggtgacc gtgacccagg atagcagcct gcaggatggc     360
gaattcatct acaaagtgaa actgcgcggc accaacttcc cgagcgatgg cccggtgatg     420
cagaaaaaga ccatgggctg ggaagcgagc agcgaacgca tgtatccgga agatggcgca     480
ctgaaaggcg aaatcaaaca gcgcctgaaa ctgaaagatg gcggtcatta tgatgcggaa     540
gtgaaaacca cctataaagc gaaaaagccg gtgcagctgc cgggtgccta acgtgaac       600
atcaaactgg atatcaccag ccataacgaa gattatacca tcgtggaaca gtatgaacgc     660
gcggaaggcc gccatagcac cggcggcatg gatgaactgt acaag                     705
```

<210> SEQ ID NO 4
<211> LENGTH: 705
<212> TYPE: DNA
<213> ORGANISM: Artificial Sequence
<220> FEATURE:
<223> OTHER INFORMATION: discosoma

<400> SEQUENCE: 4

```
atgagcaaag gcgaagagaa caacatggcg atcatcaaag agttcatgcg cttcaaagtg      60
cgcatggaag gcagcgtgaa cggccatgaa ttcgaaatcg aaggtgaagg tgaaggccgt     120
ccgtatgaag gcacccagac cgcgaaactg aaagtgacca aaggcggccc gctgccgttc     180
gcgtgggata tcctgagccc gcagttcacc tatggcagca aagcgtatgt gaaacatccg     240
accggcatcc cggattactt caaactgagc ttcccggaag cttcaaatg ggaacgcgtg      300
atgaacttcg aagatggcgg tgtggtgacc gtgacccagg atagcagcct gcaggatggc     360
gaattcatct acaaagtgaa actgcgcggc accaacttcc cgagcgatgg cccggtgatg     420
cagaaaaaga ccatgggctg ggaagcgagc agcgaacgca tgtatccgga agatggcgcg     480
ctgaaaggcg aaatcaagat gcgcctgaaa ctgaaagatg gcggccatta tagcgcggaa     540
accaaaacca cctacaaagc gaagaaaccg gtgcagctgc cgggtgcgta tcgtgggc       600
atcaaactgg atatcaccag ccataacgaa gattatacca tcgtggaaca gtatgaacgt     660
gcggaaggcc gccatagcac cggtggcatg gatgaactgt acaag                     705
```

<210> SEQ ID NO 5
<211> LENGTH: 705
<212> TYPE: DNA
<213> ORGANISM: Artificial Sequence
<220> FEATURE:
<223> OTHER INFORMATION: discosoma

<400> SEQUENCE: 5

```
atgagcaaag gcgaagaaga taacatggcg atcatcaaag agttcatgcg cttcaaattg      60
cgcatggaag gcagcgttaa cggccatgaa ttcgaaatcg aaggcgaagg cgaaggccgt     120
ccgtatgaag gcacccagac cgcgaaactg aaagtgacca aaggcggtcc gctgccgttc     180
gcgtgggata tcctgagccc gcagttctgc tatggcagca aagcgtatgt gaaacatccg     240
accggcatcc cggattactt caaactgagc ttcccggaag cttcaaatg ggaacgcatg      300
```

```
atgaacttcg aagatggcgg tgtggtgacc gtgacccagg atagcagcct gcaggatggc    360
gaattcatct acaaagtgaa actacgcggc accaacttcc cgagtgatgg cccggtgatg    420
cagaaaaaga ccatgggctg ggaagcgagc agcgaacgca tgtatccgga agatggcgcg    480
ctgaaaggcg aaatcaagat gcgcctgaaa ctgaaagatg gcggccatta tagcgcggaa    540
accaaaacca cctacaaagc gaagaaaccg gtgcagctgc cgggtgcgta tatcgtgggc    600
atcaaactgg atatcaccag ccataacgaa gattatacca tcgtggaaca gtatgaacgt    660
gcggaaggcc gccatagcac cggtggcatg gatgaactgt acaag                    705
```

<210> SEQ ID NO 6
<211> LENGTH: 238
<212> TYPE: PRT
<213> ORGANISM: Artificial Sequence
<220> FEATURE:
<223> OTHER INFORMATION: discosoma

<400> SEQUENCE: 6

```
Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 7
<211> LENGTH: 238
<212> TYPE: PRT
<213> ORGANISM: Artificial Sequence
<220> FEATURE:
<223> OTHER INFORMATION: discosoma

<400> SEQUENCE: 7

Met Ser Lys Gly Glu Glu Leu Phe Thr Gly Val Val Pro Ile Leu Val

```
            1               5                  10                 15
Glu Leu Asp Gly Asp Val Asn Gly His Lys Phe Ser Val Ser Gly Glu
             20                  25                 30

Gly Glu Gly Asp Ala Thr Tyr Gly Lys Leu Thr Leu Lys Phe Ile Cys
             35                  40                 45

Thr Thr Gly Lys Leu Pro Val Pro Trp Pro Thr Leu Val Thr Thr Leu
 50                  55                 60

Thr Tyr Gly Val Gln Cys Phe Ser Arg Tyr Pro Asp His Met Lys Gln
 65                  70                 75                 80

His Asp Phe Phe Lys Ser Ala Met Pro Glu Gly Tyr Val Gln Glu Arg
             85                  90                 95

Thr Ile Phe Tyr Lys Asp Asp Gly Asn Tyr Lys Thr Arg Ala Glu Val
             100                 105                110

Lys Phe Glu Gly Asp Thr Leu Val Asn Arg Ile Glu Leu Lys Gly Ile
             115                 120                125

Asp Phe Lys Glu Asp Gly Asn Ile Leu Gly His Lys Met Glu Tyr Asn
             130                 135                140

Phe Asn Ser His Asn Val Tyr Ile Met Gly Asp Lys Pro Lys Asn Gly
145                  150                 155                160

Ile Lys Val Asn Phe Lys Ile Arg His Asn Ile Lys Asp Gly Gly Val
                 165                 170                175

Gln Leu Ala Asp His Tyr Gln Leu Asn Thr Pro Ile Gly Asp Gly Pro
             180                 185                190

Val Ile Leu Pro Asp Asn His Tyr Leu Ser Thr Gln Ser Ala Leu Ser
             195                 200                205

Lys Asp Pro Asn Glu Lys Arg Asp His Met Val Leu Leu Glu Phe Val
             210                 215                220

Thr Ala Ala Arg Ile Thr His Gly Met Asp Glu Leu Tyr Lys
225                  230                 235
```

<210> SEQ ID NO 8
<211> LENGTH: 235
<212> TYPE: PRT
<213> ORGANISM: Artificial Sequence
<220> FEATURE:
<223> OTHER INFORMATION: discosoma

<400> SEQUENCE: 8

```
Met Ser Lys Gly Glu Glu Asp Asn Met Ala Ile Ile Lys Glu Phe Met
 1               5                  10                 15

Arg Phe Lys Val Arg Met Glu Gly Ser Val Asn Gly His Glu Phe Glu
             20                  25                 30

Ile Glu Gly Glu Gly Glu Gly Arg Pro Tyr Glu Gly Thr Gln Thr Ala
             35                  40                 45

Lys Leu Lys Val Thr Lys Gly Gly Pro Leu Pro Phe Ala Trp Asp Ile
 50                  55                 60

Leu Ser Pro Gln Phe Cys Tyr Gly Ser Lys Ala Tyr Val Lys His Pro
 65                  70                 75                 80

Ala Asp Ile Pro Asp Tyr Phe Lys Leu Ser Phe Pro Glu Gly Phe Lys
             85                  90                 95

Trp Glu Arg Met Met Asn Phe Glu Asp Gly Gly Val Val Thr Val Thr
             100                 105                110

Gln Asp Ser Ser Leu Gln Asp Gly Glu Phe Ile Tyr Lys Val Lys Leu
             115                 120                125

Arg Gly Thr Asn Phe Pro Ser Asp Gly Pro Val Met Gln Lys Lys Thr
             130                 135                140
```

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
            165                 170                 175

Tyr Asp Ala Glu Val Lys Thr Thr Tyr Lys Ala Lys Lys Pro Val Gln
            180                 185                 190

Leu Pro Gly Ala Tyr Asn Val Asn Ile Lys Leu Asp Ile Thr Ser His
            195                 200                 205

Asn Glu Asp Tyr Thr Ile Val Glu Gln Tyr Glu Arg Ala Glu Gly Arg
            210                 215                 220

His Ser Thr Gly Gly Met Asp Glu Leu Tyr Lys
225                 230                 235

<210> SEQ ID NO 9
<211> LENGTH: 235
<212> TYPE: PRT
<213> ORGANISM: Artificial Sequence
<220> FEATURE:
<223> OTHER INFORMATION: discosoma

<400> SEQUENCE: 9

Met Ser Lys Gly Glu Glu Asn Asn Met Ala Ile Ile Lys Glu Phe Met
1               5                   10                  15

Arg Phe Lys Val Arg Met Glu Gly Ser Val Asn Gly His Glu Phe Glu
            20                  25                  30

Ile Glu Gly Glu Gly Glu Gly Arg Pro Tyr Glu Gly Thr Gln Thr Ala
            35                  40                  45

Lys Leu Lys Val Thr Lys Gly Gly Pro Leu Pro Phe Ala Trp Asp Ile
50                  55                  60

Leu Ser Pro Gln Phe Thr Tyr Gly Ser Lys Ala Tyr Val Lys His Pro
65                  70                  75                  80

Thr Gly Ile Pro Asp Tyr Phe Lys Leu Ser Phe Pro Glu Gly Phe Lys
            85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
            115                 120                 125

Arg Gly Thr Asn Phe Pro Ser Asp Gly Pro Val Met Gln Lys Lys Thr
            130                 135                 140

Met Gly Trp Glu Ala Ser Ser Glu Arg Met Tyr Pro Glu Asp Gly Ala
145                 150                 155                 160

Leu Lys Gly Glu Ile Lys Met Arg Leu Lys Leu Lys Asp Gly Gly His
            165                 170                 175

Tyr Ser Ala Glu Thr Lys Thr Thr Tyr Lys Ala Lys Lys Pro Val Gln
            180                 185                 190

Leu Pro Gly Ala Tyr Ile Val Gly Ile Lys Leu Asp Ile Thr Ser His
            195                 200                 205

Asn Glu Asp Tyr Thr Ile Val Glu Gln Tyr Glu Arg Ala Glu Gly Arg
            210                 215                 220

His Ser Thr Gly Gly Met Asp Glu Leu Tyr Lys
225                 230                 235

<210> SEQ ID NO 10
<211> LENGTH: 235
<212> TYPE: PRT
<213> ORGANISM: Artificial Sequence
<220> FEATURE:

-continued

<223> OTHER INFORMATION: discosoma

<400> SEQUENCE: 10

```
Met Ser Lys Gly Glu Glu Asp Asn Met Ala Ile Ile Lys Glu Phe Met
1               5                   10                  15

Arg Phe Lys Leu Arg Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
50                  55                  60

Leu Ser Pro Gln Phe Cys Tyr Gly Ser Lys Ala Tyr Val Lys His Pro
65                  70                  75                  80

Thr Gly Ile Pro Asp Tyr Phe Lys Leu Ser Phe Pro Glu Gly Phe Lys
                85                  90                  95

Trp Glu Arg Met Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
130                 135                 140

Met Gly Trp Glu Ala Ser Ser Glu Arg Met Tyr Pro Glu Asp Gly Ala
145                 150                 155                 160

Leu Lys Gly Glu Ile Lys Met Arg Leu Lys Leu Lys Asp Gly Gly His
                165                 170                 175

Tyr Ser Ala Glu Thr Lys Thr Thr Tyr Lys Ala Lys Lys Pro Val Gln
            180                 185                 190

Leu Pro Gly Ala Tyr Ile Val Gly Ile Lys Leu Asp Ile Thr Ser His
        195                 200                 205

Asn Glu Asp Tyr Thr Ile Val Glu Gln Tyr Glu Arg Ala Glu Gly Arg
210                 215                 220

His Ser Thr Gly Gly Met Asp Glu Leu Tyr Lys
225                 230                 235
```

<210> SEQ ID NO 11
<211> LENGTH: 238
<212> TYPE: PRT
<213> ORGANISM: Artificial Sequence
<220> FEATURE:
<223> OTHER INFORMATION: aequorea victoria

<400> SEQUENCE: 11

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr His Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110
```

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Phe Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 12
<211> LENGTH: 238
<212> TYPE: PRT
<213> ORGANISM: Artificial Sequence
<220> FEATURE:
<223> OTHER INFORMATION: aequorea victoria

<400> SEQUENCE: 12

Met Ser Lys Gly Glu Glu Leu Phe Thr Gly Val Val Pro Val Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Asn Phe Ile Cys
        35                  40                  45

Thr Thr Gly Lys Leu Pro Val Pro Trp Pro Thr Leu Val Thr Thr Phe
    50                  55                  60

Ser Tyr Gly Val Met Val Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
130                 135                 140

Phe Asn Ser His Asn Val Tyr Ile Met Gly Asp Lys Pro Lys Asn Gly
145                 150                 155                 160

Ile Lys Ala Asn Phe Lys Ile Arg His Asn Ile Lys Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Ile Gln Ser Ala Leu Ser
        195                 200                 205

Lys Asp Pro Asn Glu Lys Arg Asp His Met Ile Leu Leu Glu Phe Val
210                 215                 220

Thr Ala Ala Arg Ile Thr His Gly Met Asp Glu Leu Tyr Lys
225                 230                 235
```

-continued

```
<210> SEQ ID NO 13
<211> LENGTH: 238
<212> TYPE: PRT
<213> ORGANISM: Artificial Sequence
<220> FEATURE:
<223> OTHER INFORMATION: aequorea victoria

<400> SEQUENCE: 13

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Asp Ile Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 14
<211> LENGTH: 238
<212> TYPE: PRT
<213> ORGANISM: Artificial Sequence
<220> FEATURE:
<223> OTHER INFORMATION: aequorea victoria

<400> SEQUENCE: 14

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
```

```
                    85                  90                  95
Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Ala Ile Ser Asp Ile Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 15
<211> LENGTH: 238
<212> TYPE: PRT
<213> ORGANISM: Artificial Sequence
<220> FEATURE:
<223> OTHER INFORMATION: aequorea victoria

<400> SEQUENCE: 15

Met Ser Lys Gly Glu Glu Leu Phe Gly Gly Val Ile Pro Val Leu Val
1               5                   10                  15

Glu Leu Glu Gly Asp Val Asn Gly Gln Lys Phe Ser Val Ser Gly Glu
            20                  25                  30

Gly Glu Gly Asp Ala Thr Tyr Gly Lys Leu Thr Leu Asn Phe Ile Cys
        35                  40                  45

Thr Thr Gly Lys Leu Pro Val Pro Trp Pro Thr Leu Val Thr Thr Leu
    50                  55                  60

Thr Trp Gly Val Gln Cys Phe Ser Arg Tyr Pro Asp His Met Lys Gln
65                  70                  75                  80

His Asp Phe Phe Lys Ser Val Met Pro Glu Gly Tyr Val Gln Glu Arg
                85                  90                  95

Thr Ile Phe Tyr Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Met Glu Tyr Asn
        130                 135                 140

Tyr Asn Ser His Ile Val Tyr Ile Thr Gly Asp Lys Pro Lys Asn Gly
145                 150                 155                 160

Ile Lys Ala Asn Phe Lys Ala Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Ile Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
210                 215                 220
```

```
Thr Ala Ala Arg Ile Thr His Gly Met Asp Glu Leu Tyr Lys
225                 230                 235
```

<210> SEQ ID NO 16
<211> LENGTH: 238
<212> TYPE: PRT
<213> ORGANISM: Artificial Sequence
<220> FEATURE:
<223> OTHER INFORMATION: aequorea victoria

<400> SEQUENCE: 16

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 17
<211> LENGTH: 238
<212> TYPE: PRT
<213> ORGANISM: Artificial Sequence
<220> FEATURE:
<223> OTHER INFORMATION: aequorea victoria

<400> SEQUENCE: 17

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60
```

```
Thr Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 18
<211> LENGTH: 238
<212> TYPE: PRT
<213> ORGANISM: Artificial Sequence
<220> FEATURE:
<223> OTHER INFORMATION: aequorea victoria

<400> SEQUENCE: 18

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Leu
     50                  55                  60

Gly His Gly Val Gln Cys Phe Ala Arg Tyr Pro Asp His Met Arg Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Phe Asn Ser His Asn Val Tyr Ile Met Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190
```

```
Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 19
<211> LENGTH: 238
<212> TYPE: PRT
<213> ORGANISM: Artificial Sequence
<220> FEATURE:
<223> OTHER INFORMATION: aequorea victoria

<400> SEQUENCE: 19

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 20
<211> LENGTH: 238
<212> TYPE: PRT
<213> ORGANISM: Artificial Sequence
<220> FEATURE:
<223> OTHER INFORMATION: aequorea victoria

<400> SEQUENCE: 20

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30
```

```
Gly Glu Gly Asp Ala Thr Tyr Gly Lys Leu Thr Leu Lys Leu Ile Cys
             35                  40                  45

Thr Thr Gly Lys Leu Pro Val Pro Trp Pro Thr Leu Val Thr Thr Leu
 50                  55                  60

Gly Tyr Gly Leu Gln Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 21
<211> LENGTH: 238
<212> TYPE: PRT
<213> ORGANISM: Artificial Sequence
<220> FEATURE:
<223> OTHER INFORMATION: aequorea victoria

<400> SEQUENCE: 21

Met Ser Lys Gly Glu Glu Leu Phe Thr Gly Val Val Pro Val Leu Val
 1               5                  10                  15

Glu Leu Asp Gly Asp Val Asn Gly Gln Lys Phe Ser Val Ser Gly Glu
             20                  25                  30

Gly Glu Gly Asp Ala Thr Tyr Gly Lys Leu Thr Leu Asn Phe Ile Cys
             35                  40                  45

Thr Thr Gly Lys Leu Pro Val Pro Trp Pro Thr Leu Val Thr Thr Phe
 50                  55                  60

Gly Tyr Gly Leu Met Cys Phe Ala Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
130                 135                 140

Tyr Asn Ser His Asn Val Tyr Ile Met Gly Asp Lys Pro Lys Asn Gly
145                 150                 155                 160

Ile Lys Val Asn Phe Lys Ile Arg His Asn Ile Lys Asp Gly Ser Val
```

-continued

Gln Leu Ala Asp His Tyr Gln Gln Asn Thr Pro Ile Gly Asp Gly Pro
        165                 170                 175
Val Leu Leu Pro Asp Asn His Tyr Leu Ser Tyr Gln Ser Lys Leu Ser
    180                 185                 190
Lys Asp Pro Asn Glu Lys Arg Asp His Met Ile Leu Leu Glu Phe Val
195                 200                 205
Thr Ala Ala Arg Ile Thr His Gly Met Asp Glu Leu Tyr Lys
210                 215                 220
        225                 230                 235

<210> SEQ ID NO 22
<211> LENGTH: 238
<212> TYPE: PRT
<213> ORGANISM: Artificial Sequence
<220> FEATURE:
<223> OTHER INFORMATION: aequorea victoria

<400> SEQUENCE: 22

Met Ser Lys Gly Glu Glu Leu Phe Thr Gly Val Val Pro Val Leu Val
1               5                   10                  15
Glu Leu Asp Gly Asp Val Asn Gly Gln Lys Phe Ser Val Ser Gly Glu
            20                  25                  30
Gly Glu Gly Asp Ala Thr Tyr Gly Lys Leu Thr Leu Asn Leu Leu Cys
        35                  40                  45
Thr Thr Gly Lys Leu Pro Val Pro Trp Pro Thr Leu Val Thr Thr Leu
    50                  55                  60
Gly Tyr Gly Val Gln Cys Phe Ala Arg Tyr Pro Asp His Met Lys Gln
65                  70                  75                  80
His Asp Phe Phe Lys Ser Ala Met Pro Glu Gly Tyr Val Gln Glu Arg
                85                  90                  95
Thr Ile Phe Tyr Lys Asp Asp Gly Asn Tyr Lys Thr Arg Ala Glu Val
            100                 105                 110
Lys Phe Glu Gly Asp Thr Leu Val Asn Arg Ile Glu Leu Lys Gly Ile
        115                 120                 125
Asp Phe Lys Glu Asp Gly Asn Ile Leu Gly His Lys Met Glu Tyr Asn
    130                 135                 140
Tyr Asn Ser His Asn Val Tyr Ile Thr Gly Asp Lys Pro Lys Asn Gly
145                 150                 155                 160
Ile Lys Ala Asn Phe Lys Ile Arg His Asn Ile Lys Asp Gly Gly Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Tyr Gln Ser Ala Leu Phe
        195                 200                 205
Lys Asp Pro Asn Glu Lys Arg Asp His Met Ile Leu Leu Glu Phe Leu
    210                 215                 220
Thr Ala Ala Arg Ile Thr Glu Gly Met Asn Glu Leu Tyr Lys
225                 230                 235

<210> SEQ ID NO 23
<211> LENGTH: 235
<212> TYPE: PRT
<213> ORGANISM: Artificial Sequence
<220> FEATURE:
<223> OTHER INFORMATION: aequorea victoria

<400> SEQUENCE: 23

Met Ser Lys Gly Glu Glu Asn Asn Met Ala Val Ile Lys Glu Phe Met

```
            1               5                  10                 15
Arg Phe Lys Val Arg Met Glu Gly Ser Val Asn Gly His Glu Phe Glu
            20                 25                 30

Ile Glu Gly Glu Gly Glu Gly Arg Pro Tyr Glu Gly Thr Gln Thr Ala
            35                 40                 45

Lys Leu Lys Val Thr Lys Gly Gly Pro Leu Pro Phe Ala Trp Asp Ile
            50                 55                 60

Leu Ser Pro Gln Phe Cys Tyr Gly Ser Lys Ala Tyr Val Lys His Pro
65                 70                 75                     80

Thr Gly Ile Pro Asp Tyr Phe Lys Leu Ser Phe Pro Glu Gly Phe Lys
                85                 90                 95

Trp Glu Arg Val Met Asn Phe Glu Asp Gly Gly Val Val Thr Val Ala
                100                105                110

Gln Asp Ser Ser Leu Gln Asp Gly Glu Phe Ile Tyr Lys Val Lys Leu
                115                120                125

Arg Gly Thr Asn Phe Pro Ser Asp Gly Pro Val Met Gln Lys Lys Thr
            130                135                140

Met Gly Trp Glu Ala Ser Ser Glu Arg Met Tyr Pro Glu Asp Gly Ala
145                150                155                    160

Leu Lys Gly Glu Ile Lys Met Arg Leu Lys Leu Lys Asp Gly Gly His
                165                170                175

Tyr Ser Ala Glu Thr Lys Thr Thr Tyr Lys Ala Lys Lys Pro Val Gln
                180                185                190

Leu Pro Gly Ala Tyr Ile Ala Gly Glu Lys Ile Asp Ile Thr Ser His
                195                200                205

Asn Glu Asp Tyr Thr Ile Val Glu Leu Tyr Glu Arg Ala Glu Gly Arg
            210                215                220

His Ser Thr Gly Gly Met Asp Glu Leu Tyr Lys
225                230                235

<210> SEQ ID NO 24
<211> LENGTH: 235
<212> TYPE: PRT
<213> ORGANISM: Artificial Sequence
<220> FEATURE:
<223> OTHER INFORMATION: aequorea victoria

<400> SEQUENCE: 24

Met Ser Lys Gly Glu Glu Asn Asn Met Ala Ile Ile Lys Glu Phe Met
1               5                  10                 15

Arg Phe Lys Val Arg Met Glu Gly Ser Val Asn Gly His Glu Phe Glu
            20                 25                 30

Ile Glu Gly Glu Gly Glu Gly Arg Pro Tyr Glu Gly Phe Gln Thr Ala
            35                 40                 45

Lys Leu Lys Val Thr Lys Gly Gly Pro Leu Pro Phe Ala Trp Asp Ile
            50                 55                 60

Leu Ser Pro Gln Phe Thr Tyr Gly Ser Lys Ala Tyr Val Lys His Pro
65                 70                 75                     80

Ala Asp Ile Pro Asp Tyr Phe Lys Leu Ser Phe Pro Glu Gly Phe Lys
                85                 90                 95

Trp Glu Arg Val Met Asn Phe Glu Asp Gly Gly Val Val Thr Val Thr
                100                105                110

Gln Asp Ser Ser Leu Gln Asp Gly Glu Phe Ile Tyr Lys Val Lys Leu
                115                120                125

Arg Gly Thr Asn Phe Pro Ser Asp Gly Pro Val Met Gln Lys Lys Thr
            130                135                140
```

```
Met Gly Trp Glu Ala Ser Ser Glu Arg Met Tyr Pro Glu Asp Gly Ala
145                 150                 155                 160

Leu Lys Gly Glu Ile Lys Met Arg Leu Lys Leu Lys Asp Gly Gly His
            165                 170                 175

Tyr Thr Ser Glu Val Lys Thr Thr Tyr Lys Ala Lys Lys Pro Val Gln
            180                 185                 190

Leu Pro Gly Ala Tyr Ile Val Gly Ile Lys Leu Asp Ile Thr Ser His
            195                 200                 205

Asn Glu Asp Tyr Thr Ile Val Glu Gln Tyr Glu Arg Ala Glu Gly Arg
            210                 215                 220

His Ser Thr Gly Gly Met Asp Glu Leu Tyr Lys
225                 230                 235

<210> SEQ ID NO 25
<211> LENGTH: 233
<212> TYPE: PRT
<213> ORGANISM: Artificial Sequence
<220> FEATURE:
<223> OTHER INFORMATION: aequorea victoria

<400> SEQUENCE: 25

Met Ser Lys Gly Glu Glu Val Ile Lys Glu Phe Met Arg Phe Lys Val
1               5                   10                  15

Arg Met Glu Gly Ser Met Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
50                  55                  60

Phe Met Tyr Gly Ser Lys Ala Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Leu Val Thr Val Thr Gln Asp Ser Ser
            100                 105                 110

Leu Gln Asp Gly Thr Leu Ile Tyr Lys Val Lys Met Arg Gly Thr Asn
        115                 120                 125

Phe Pro Pro Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Gln Ala Leu Lys Leu Lys Asp Gly Gly His Tyr Leu Val Glu
            165                 170                 175

Phe Lys Thr Ile Tyr Met Ala Lys Lys Pro Val Gln Leu Pro Gly Tyr
            180                 185                 190

Tyr Tyr Val Asp Thr Lys Leu Asp Ile Thr Ser His Asn Glu Asp Tyr
            195                 200                 205

Thr Ile Val Glu Gln Tyr Glu Arg Ser Glu Gly Arg His His Leu Phe
210                 215                 220

Leu Tyr Gly Met Asp Glu Leu Tyr Lys
225                 230

<210> SEQ ID NO 26
<211> LENGTH: 235
<212> TYPE: PRT
<213> ORGANISM: Artificial Sequence
<220> FEATURE:
```

<223> OTHER INFORMATION: aequorea victoria

<400> SEQUENCE: 26

```
Met Ser Lys Gly Glu Glu Asn Asn Met Ala Ile Ile Lys Glu Phe Met
1               5                   10                  15

Arg Phe Lys Val Arg Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
50                  55                  60

Leu Thr Pro Asn Phe Thr Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
130                 135                 140

Met Gly Trp Glu Ala Ser Ser Glu Arg Met Tyr Pro Glu Asp Gly Ala
145                 150                 155                 160

Leu Lys Gly Glu Ile Lys Met Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190

Leu Pro Gly Ala Tyr Ile Val Gly Ile Lys Leu Asp Ile Thr Ser His
        195                 200                 205

Asn Glu Asp Tyr Thr Ile Val Glu Leu Tyr Glu Arg Ala Glu Gly Arg
210                 215                 220

His Ser Thr Gly Gly Met Asp Glu Leu Tyr Lys
225                 230                 235
```

<210> SEQ ID NO 27
<211> LENGTH: 235
<212> TYPE: PRT
<213> ORGANISM: Artificial Sequence
<220> FEATURE:
<223> OTHER INFORMATION: aequorea victoria

<400> SEQUENCE: 27

```
Met Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110
```

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
                180                 185                 190

Leu Pro Gly Ala Tyr Asn Val Asn Ile Lys Leu Asp Ile Thr Ser His
            195                 200                 205

Asn Glu Asp Tyr Thr Ile Val Glu Gln Tyr Glu Arg Ala Glu Gly Arg
210                 215                 220

His Ser Thr Gly Gly Met Asp Glu Leu Tyr Lys
225                 230                 235

<210> SEQ ID NO 28
<211> LENGTH: 238
<212> TYPE: PRT
<213> ORGANISM: Artificial Sequence
<220> FEATURE:
<223> OTHER INFORMATION: aequorea victoria

<400> SEQUENCE: 28

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Phe Asn Ser His Asn Val Tyr Ile Met Gly Asp Lys Pro Lys Asn Gly
145                 150                 155                 160

Ile Lys Val Asn Phe Lys Ile Arg His Asn Ile Lys Asp Gly Gly Val
                165                 170                 175

Gln Leu Ala Asp His Tyr Gln Leu Asn Thr Pro Ile Gly Asp Gly Pro
            180                 185                 190

Val Ile Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Arg Ile Thr His Gly Met Asp Glu Leu Tyr Lys
225                 230                 235

```
<210> SEQ ID NO 29
<211> LENGTH: 238
<212> TYPE: PRT
<213> ORGANISM: Artificial Sequence
<220> FEATURE:
<223> OTHER INFORMATION: aequorea victoria

<400> SEQUENCE: 29

Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 30
<211> LENGTH: 235
<212> TYPE: PRT
<213> ORGANISM: Artificial Sequence
<220> FEATURE:
<223> OTHER INFORMATION: aequorea victoria

<400> SEQUENCE: 30

Met Ser Lys Gly Glu Glu Asp Asn Met Ala Ile Ile Lys Glu Phe Met
1               5                   10                  15

Arg Phe Lys Val Arg Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
    50                  55                  60

Leu Ser Pro Gln Phe Cys Tyr Gly Ser Lys Ala Tyr Val Lys His Pro
65                  70                  75                  80

Ala Asp Ile Pro Asp Tyr Phe Lys Leu Ser Phe Pro Glu Gly Phe Lys
```

```
                        85                  90                  95
Trp Glu Arg Met Met Asn Phe Glu Asp Gly Val Val Thr Val Thr
                100                 105                 110
Gln Asp Ser Ser Leu Gln Asp Gly Glu Phe Ile Tyr Lys Val Lys Leu
                115                 120                 125
Arg Gly Thr Asn Phe Pro Ser Asp Gly Pro Val Met Gln Lys Lys Thr
                130                 135                 140
Met Gly Trp Glu Ala Ser Ser Glu Arg Met Tyr Pro Glu Asp Gly Ala
145                 150                 155                 160
Leu Lys Gly Glu Ile Lys Gln Arg Leu Lys Leu Lys Asp Gly Gly His
                165                 170                 175
Tyr Asp Ala Glu Val Lys Thr Thr Tyr Lys Ala Lys Lys Pro Val Gln
                180                 185                 190
Leu Pro Gly Ala Tyr Asn Val Asn Ile Lys Leu Asp Ile Thr Ser His
                195                 200                 205
Asn Glu Asp Tyr Thr Ile Val Glu Gln Tyr Glu Arg Ala Glu Gly Arg
                210                 215                 220
His Ser Thr Gly Gly Met Asp Glu Leu Tyr Lys
225                 230                 235

<210> SEQ ID NO 31
<211> LENGTH: 235
<212> TYPE: PRT
<213> ORGANISM: Artificial Sequence
<220> FEATURE:
<223> OTHER INFORMATION: aequorea victoria

<400> SEQUENCE: 31

Met Ser Lys Gly Glu Glu Asn Asn Met Ala Ile Ile Lys Glu Phe Met
1               5                   10                  15
Arg Phe Lys Val Arg Met Glu Gly Ser Val Asn Gly His Glu Phe Glu
                20                  25                  30
Ile Glu Gly Glu Gly Glu Gly Arg Pro Tyr Glu Gly Thr Gln Thr Ala
                35                  40                  45
Lys Leu Lys Val Thr Lys Gly Gly Pro Leu Pro Phe Ala Trp Asp Ile
                50                  55                  60
Leu Ser Pro Gln Phe Thr Tyr Gly Ser Lys Ala Tyr Val Lys His Pro
65                  70                  75                  80
Thr Gly Ile Pro Asp Tyr Phe Lys Leu Ser Phe Pro Glu Gly Phe Lys
                85                  90                  95
Trp Glu Arg Val Met Asn Phe Glu Asp Gly Gly Val Val Thr Val Thr
                100                 105                 110
Gln Asp Ser Ser Leu Gln Asp Gly Glu Phe Ile Tyr Lys Val Lys Leu
                115                 120                 125
Arg Gly Thr Asn Phe Pro Ser Asp Gly Pro Val Met Gln Lys Lys Thr
                130                 135                 140
Met Gly Trp Glu Ala Ser Ser Glu Arg Met Tyr Pro Glu Asp Gly Ala
145                 150                 155                 160
Leu Lys Gly Glu Ile Lys Met Arg Leu Lys Leu Lys Asp Gly Gly His
                165                 170                 175
Tyr Ser Ala Glu Thr Lys Thr Thr Tyr Lys Ala Lys Lys Pro Val Gln
                180                 185                 190
Leu Pro Gly Ala Tyr Ile Val Gly Ile Lys Leu Asp Ile Thr Ser His
                195                 200                 205
Asn Glu Asp Tyr Thr Ile Val Glu Gln Tyr Glu Arg Ala Glu Gly Arg
                210                 215                 220
```

```
His Ser Thr Gly Gly Met Asp Glu Leu Tyr Lys
225                 230                 235

<210> SEQ ID NO 32
<211> LENGTH: 235
<212> TYPE: PRT
<213> ORGANISM: Artificial Sequence
<220> FEATURE:
<223> OTHER INFORMATION: aequorea victoria

<400> SEQUENCE: 32

Met Ser Lys Gly Glu Glu Asp Asn Met Ala Ile Ile Lys Glu Phe Met
1               5                   10                  15

Arg Phe Lys Leu Arg Met Glu Gly Ser Val Asn Gly His Glu Phe Glu
                20                  25                  30

Ile Glu Gly Glu Gly Glu Gly Arg Pro Tyr Glu Gly Thr Gln Thr Ala
            35                  40                  45

Lys Leu Lys Val Thr Lys Gly Gly Pro Leu Pro Phe Ala Trp Asp Ile
    50                  55                  60

Leu Ser Pro Gln Phe Cys Tyr Gly Ser Lys Ala Tyr Val Lys His Pro
65                  70                  75                  80

Thr Gly Ile Pro Asp Tyr Phe Lys Leu Ser Phe Pro Glu Gly Phe Lys
                85                  90                  95

Trp Glu Arg Met Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
    130                 135                 140

Met Gly Trp Glu Ala Ser Ser Glu Arg Met Tyr Pro Glu Asp Gly Ala
145                 150                 155                 160

Leu Lys Gly Glu Ile Lys Met Arg Leu Lys Leu Lys Asp Gly Gly His
                165                 170                 175

Tyr Ser Ala Glu Thr Lys Thr Thr Tyr Lys Ala Lys Lys Pro Val Gln
            180                 185                 190

Leu Pro Gly Ala Tyr Ile Val Gly Ile Lys Leu Asp Ile Thr Ser His
        195                 200                 205

Asn Glu Asp Tyr Thr Ile Val Glu Gln Tyr Glu Arg Ala Glu Gly Arg
    210                 215                 220

His Ser Thr Gly Gly Met Asp Glu Leu Tyr Lys
225                 230                 235

<210> SEQ ID NO 33
<211> LENGTH: 238
<212> TYPE: PRT
<213> ORGANISM: Artificial Sequence
<220> FEATURE:
<223> OTHER INFORMATION: aequorea victoria

<400> SEQUENCE: 33

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Cys Asp Ala Thr Tyr Gly Lys Leu Thr Leu Asn Phe Ile Cys
            35                  40                  45

Thr Thr Gly Lys Leu Pro Val Pro Trp Pro Thr Leu Val Thr Thr Phe
    50                  55                  60
```

Gly Tyr Gly Leu Met Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Asp Ile Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Ser Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 34
<211> LENGTH: 238
<212> TYPE: PRT
<213> ORGANISM: Artificial Sequence
<220> FEATURE:
<223> OTHER INFORMATION: aequorea victoria

<400> SEQUENCE: 34

Met Ser Lys Gly Glu Glu Leu Phe Thr Gly Val Val Pro Ile Leu Val
1               5                   10                  15

Glu Leu Asp Ser Asp Val Asn Gly His Lys Phe Ser Val Ser Gly Glu
                20                  25                  30

Gly Glu Gly Asp Ala Thr Tyr Gly Lys Leu Thr Leu Asn Phe Ile Cys
            35                  40                  45

Thr Thr Gly Lys Leu Pro Val Pro Trp Pro Thr Leu Val Thr Thr Leu
        50                  55                  60

Gly His Cys Val Gln Cys Phe Ala Arg Tyr Pro Asp His Met Arg Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Asp Ile Val Tyr Ile Thr Ala Asp Lys Gln Lys Asn Gly
145                 150                 155                 160

Ile Lys Ala Asn Phe Lys Ile Arg His Asn Ile Lys Asp Gly Gly Val
                165                 170                 175

Gln Leu Ala Asp His Tyr Gln Gln Asn Thr Pro Ile Gly Asp Gly Pro
            180                 185                 190

```
Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 35
<211> LENGTH: 238
<212> TYPE: PRT
<213> ORGANISM: Artificial Sequence
<220> FEATURE:
<223> OTHER INFORMATION: aequorea victoria

<400> SEQUENCE: 35

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Arg Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Cys Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Ile Val Tyr Ile Thr Gly Asp Lys Pro Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Leu Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 36
<211> LENGTH: 233
<212> TYPE: PRT
<213> ORGANISM: Artificial Sequence
<220> FEATURE:
<223> OTHER INFORMATION: aequorea victoria

<400> SEQUENCE: 36

Met Ser Lys Gly Glu Glu Leu Phe Gly Gly Val Ile Pro Val Leu Val
1               5                   10                  15

Glu Leu Glu Gly Asp Val Asn Gly Gln Lys Phe Ser Val Ser Gly Glu
            20                  25                  30
```

Gly Glu Gly Glu Gly Arg Pro Tyr Glu Gly Phe Gln Thr Ala Lys Leu
             35                  40                  45

Lys Val Thr Lys Gly Gly Pro Leu Pro Phe Ala Trp Asp Ile Leu Ser
 50                  55                  60

Pro Gln Phe Cys Tyr Gly Ser Lys Ala Tyr Val Lys His Pro Ala Asp
 65                  70                  75                  80

Ile Pro Asp Tyr Leu Lys Leu Ser Phe Pro Glu Gly Phe Lys Trp Glu
             85                  90                  95

Arg Met Met Asn Phe Glu Asp Gly Gly Val Met Thr Val Ala Gln Asp
                100                 105                 110

Ser Ser Leu Gln Asp Gly Glu Phe Ile Tyr Lys Val Lys Leu Arg Gly
            115                 120                 125

Thr Asn Phe Pro Ser Asp Gly Pro Val Met Gln Lys Lys Thr Met Cys
130                 135                 140

Trp Glu Ala Ser Ser Glu Arg Met Tyr Pro Glu Asp Gly Ala Leu Lys
145                 150                 155                 160

Gly Glu Ile Lys Gln Arg Leu Lys Leu Lys Asp Gly His Tyr Asp
                165                 170                 175

Ala Glu Val Lys Thr Thr Tyr Lys Ala Lys Lys Pro Val Gln Leu Pro
            180                 185                 190

Gly Ala Tyr Ile Val Gly Ile Lys Leu Asp Ile Thr Ser His Asn Glu
195                 200                 205

Asp Tyr Thr Ile Val Glu Gln Tyr Glu Arg Ala Glu Gly Arg His Ser
    210                 215                 220

Thr Gly Gly Met Asp Glu Leu Tyr Lys
225                 230

<210> SEQ ID NO 37
<211> LENGTH: 238
<212> TYPE: PRT
<213> ORGANISM: Artificial Sequence
<220> FEATURE:
<223> OTHER INFORMATION: aequorea victoria

<400> SEQUENCE: 37

Met Ser Lys Gly Glu Glu Leu Phe Thr Gly Val Val Pro Val Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Gln Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Glu Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Cys Asn
    130                 135                 140

Phe Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val

```
                    165                 170                 175
Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
            195                 200                 205

Lys Asp Pro Asn Glu Lys Arg Asn His Met Val Leu Leu Glu Phe Val
210                 215                 220

Thr Ala Ala Gly Ile Thr Leu Gly Ile Asp Glu Leu Tyr Lys
225                 230                 235

<210> SEQ ID NO 38
<211> LENGTH: 235
<212> TYPE: PRT
<213> ORGANISM: Artificial Sequence
<220> FEATURE:
<223> OTHER INFORMATION: aequorea victoria

<400> SEQUENCE: 38

Met Ser Lys Gly Glu Glu Asn Asn Met Ala Val Ile Lys Glu Phe Met
1               5                   10                  15

Arg Phe Lys Val Arg Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
    50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Met Met Asn Leu Glu Asp Gly Gly Val Val Thr Val Thr
            100                 105                 110

Gln Asp Ser Ser Leu Gln Asp Gly Glu Phe Ile Asn Lys Val Lys Leu
        115                 120                 125

Arg Gly Thr Asn Phe Pro Ser Asp Gly Pro Val Met Gln Lys Lys Thr
    130                 135                 140

Met Ser Trp Glu Ala Ser Ser Glu Arg Met Tyr Pro Glu Asp Gly Ala
145                 150                 155                 160

Leu Lys Gly Glu Ile Lys Met Arg Leu Lys Leu Lys Asp Gly Gly Gln
                165                 170                 175

Tyr Ser Ala Glu Thr Lys Thr Thr Tyr Lys Ala Lys Lys Pro Val Gln
            180                 185                 190

Leu Pro Gly Ala Tyr Ile Val Gly Ile Lys Leu Asp Ile Thr Ser His
        195                 200                 205

Asn Glu Asp Tyr Thr Ile Val Glu Gln Tyr Glu Arg Ala Glu Gly Arg
    210                 215                 220

His Ser Thr Gly Gly Met Asp Glu Leu Tyr Lys
225                 230                 235

<210> SEQ ID NO 39
<211> LENGTH: 238
<212> TYPE: PRT
<213> ORGANISM: Artificial Sequence
<220> FEATURE:
<223> OTHER INFORMATION: aequorea victoria

<400> SEQUENCE: 39

Met Ser Lys Gly Glu Glu Leu Phe Thr Gly Val Val Pro Val Leu Val
```

```
                1               5                  10                 15
Glu Leu Asp Gly Asp Val Asn Gly Gln Lys Phe Ser Val Ser Gly Glu
                20                  25                  30

Gly Glu Gly Asp Ala Thr Tyr Gly Lys Leu Thr Leu Lys Phe Ile Cys
                35                  40                  45

Thr Thr Gly Lys Leu Arg Val Pro Trp Pro Thr Leu Val Thr Thr Leu
    50                  55                  60

Gly Tyr Gly Leu Gln Cys Phe Ser Arg Tyr Pro Asp His Met Lys Gln
65                  70                  75                  80

His Asp Phe Phe Lys Ser Ala Met Pro Glu Ser Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Phe Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Thr Asp His Tyr Gln Gln Asn Thr Pro Ile Gly Asp Gly Pro
            180                 185                 190

Val Leu Leu Pro Asp Asn His Tyr Leu Ser Thr Gln Ser Thr Leu Ser
            195                 200                 205

Lys Asp Pro Asn Glu Lys Arg Asp His Met Val Leu Leu Glu Phe Val
        210                 215                 220

Thr Ala Ala Gly Ile Thr Leu Gly Met Asp Glu Leu Tyr Lys
225                 230                 235

<210> SEQ ID NO 40
<211> LENGTH: 238
<212> TYPE: PRT
<213> ORGANISM: Artificial Sequence
<220> FEATURE:
<223> OTHER INFORMATION: aequorea victoria

<400> SEQUENCE: 40

Met Ser Lys Gly Glu Glu Leu Phe Thr Gly Val Val Pro Ile Leu Leu
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
                35                  40                  45

Thr Thr Gly Lys Leu Pro Val Pro Trp Pro Thr Leu Val Thr Thr Phe
    50                  55                  60

Ser His Gly Val Gln Tyr Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Ser
        130                 135                 140
```

Tyr Asn Ser His Asn Val Tyr Ile Met Gly Asp Lys Pro Lys Asn Gly
145                 150                 155                 160

Ile Lys Val Asn Phe Lys Ile Arg His Asn Ile Lys Asp Gly Gly Val
            165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Ser Thr Gln Ser Ala Leu Ser
    195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 41
<211> LENGTH: 238
<212> TYPE: PRT
<213> ORGANISM: Artificial Sequence
<220> FEATURE:
<223> OTHER INFORMATION: aequorea victoria

<400> SEQUENCE: 41

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Gln Val Pro Trp Pro Thr Leu Val Thr Thr Leu
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Ile Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
130                 135                 140

Tyr Asn Ser His Asn Val Tyr Ile Met Ala Asp Lys Gln Lys Asp Gly
145                 150                 155                 160

Ile Lys Val Asn Phe Lys Ile Arg His Asn Ile Glu Asp Gly Gly Val
            165                 170                 175

Gln Leu Ala Asp His Tyr Gln Leu Asn Thr Pro Ile Gly Asp Gly Pro
        180                 185                 190

Val Leu Leu Pro Asp Asn His Tyr Leu Ser Tyr Gln Ser Ala Leu Ser
    195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 42
<211> LENGTH: 238
<212> TYPE: PRT
<213> ORGANISM: Artificial Sequence
<220> FEATURE:

-continued

<223> OTHER INFORMATION: aequorea victoria

<400> SEQUENCE: 42

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Ala Ile Ser Asp Ile Val Tyr Ile Thr Ala Asp Lys Gln Lys Asn Gly
145                 150                 155                 160

Ile Lys Ala Asn Phe Lys Ala Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
210                 215                 220

Thr Thr Ala Gly Ile Thr Leu Gly Met Asp Glu Leu Tyr Lys
225                 230                 235

<210> SEQ ID NO 43
<211> LENGTH: 238
<212> TYPE: PRT
<213> ORGANISM: Artificial Sequence
<220> FEATURE:
<223> OTHER INFORMATION: aequorea victoria

<400> SEQUENCE: 43

Met Ser Lys Gly Glu Glu Leu Phe Thr Gly Val Val Pro Val Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Ala Ile Ser Asp Ile Val Tyr Ile Thr Ala Asp Lys Gln Lys Asn Gly
145                 150                 155                 160

Ile Lys Ala Asn Phe Lys Ile Arg His Asn Ile Glu Asp Gly Gly Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 44
<211> LENGTH: 238
<212> TYPE: PRT
<213> ORGANISM: Artificial Sequence
<220> FEATURE:
<223> OTHER INFORMATION: aequorea victoria

<400> SEQUENCE: 44

Met Ser Lys Gly Glu Glu Leu Phe Thr Gly Val Val Pro Ile Leu Val
1               5                   10                  15

Glu Leu Asp Ser Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Arg Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Ala Ile Ser Asp Ile Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Gln Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```

```
<210> SEQ ID NO 45
<211> LENGTH: 238
<212> TYPE: PRT
<213> ORGANISM: Artificial Sequence
<220> FEATURE:
<223> OTHER INFORMATION: aequorea victoria

<400> SEQUENCE: 45

Met Ser Lys Gly Glu Glu Leu Phe Thr Gly Val Val Pro Ile Leu Val
1               5                   10                  15

Glu Leu Asp Ser Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Arg Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Ala Ile Ser Asp Ile Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Gln Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235
```